United States Patent
Balkovec et al.

(12)

(10) Patent No.: US 6,864,278 B2
(45) Date of Patent: Mar. 8, 2005

(54) ANTIFUNGAL AGENTS OF SORDARIN DERIVATIVES

(75) Inventors: James M. Balkovec, Martinsville, NJ (US); Bruno Tse, San Diego, CA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/484,234

(22) PCT Filed: Jul. 12, 2002

(86) PCT No.: PCT/US02/22152

§ 371 (c)(1),
(2), (4) Date: Jan. 16, 2004

(87) PCT Pub. No.: WO03/007878

PCT Pub. Date: Jan. 30, 2003

(65) Prior Publication Data

US 2004/0171675 A1 Sep. 2, 2004

Related U.S. Application Data

(60) Provisional application No. 60/306,358, filed on Jul. 18, 2001.

(51) Int. Cl.$^7$ ............... C07C 69/753; C07C 69/757; A61K 31/19
(52) U.S. Cl. ............ 514/456; 514/460; 514/473; 514/529; 514/572; 504/320; 549/396; 549/416; 549/449; 560/116; 562/498
(58) Field of Search ...................... 514/456, 460, 514/473, 529, 572; 504/320; 549/396, 416, 449; 560/116; 562/498

(56) References Cited

U.S. PATENT DOCUMENTS

| 5,965,612 A | 10/1999 | Tse |
| 5,972,996 A | 10/1999 | Nielse-Kahn et al. |
| 6,136,853 A | 10/2000 | Balkovec et al. |
| 6,228,622 B1 | 5/2001 | Sturr et al. |

FOREIGN PATENT DOCUMENTS

| GB | 1162027 | 8/1969 |
| JP | 06157582 | 6/1994 |
| JP | 06240292 | 8/1994 |
| JP | 2001097991 | 4/2001 |
| WO | WO 96/14326 | 5/1996 |
| WO | WO 96/14327 | 5/1996 |

OTHER PUBLICATIONS

Helvetica Chimica Acta, 1971, 54, (4):119–20.

J. Antibiotics, 1995, 48:1171–1172.

J. Org. Chem., 1991, 56(11):3395–3601.

J. Chem. Soc., Chem. Commun., 1993, 1002–1004.

Primary Examiner—Bernard Dentz
(74) Attorney, Agent, or Firm—Min Wang; Valerie J. Camara

(57) ABSTRACT

Sordarin derivatives prepared from C-11-hydroxysordarin are antifungal agents useful in the treatment and/or prevention of human and animal fungal infections, as well as in the control of phytopathogenic fungi in crops.

24 Claims, No Drawings

ANTIFUNGAL AGENTS OF SORDARIN DERIVATIVES

This application is the National Stage of International Application No. PCT/US02/22152, filed on Jul. 12, 2002, which claims the benefit under 35 U.S.C. 119(e) of U.S. Provisional Application No. 60/306,358 filed on Jul. 18, 2001.

FIELD OF INVENTION

The present invention relates to a class of novel compounds derived from C-11-hydroxysordarin that are useful as an antifungal agent.

BACKGROUND OF THE INVENTION

Sordarin is an antifungal antibiotic isolated from the mould *Sordaria araneosa* (see GB 1,162,027 and *Helvetica Chimica Acta*, 1971, 51:119–20). Other compounds having the sordarin skeleton have also been reported as antifungal agents. Japanese Kokai J62040292 discloses the compound zofimarin isolated from *Zofiela marina* sp.; Japanese Kokai J06157582 discloses the compound BE-31405 isolated from *Penicillium* sp.; and SCH57404 is reported in *J. Antibiotics*, 1995, 48:1171–1172. Semi-synthetic sordarin derivatives are reported in PCT Applications WO96/14326 and WO96/14327.

Sordaricin, the aglycone, may be obtained from sordarin by acid hydrolysis (Hauser and Sigg, *Helvetica Chimica Acta*, 1971, 51:119–20). The total synthesis of sordaricin methyl ester is reported in Kato et al., *J. Chem. Soc., Chem. Commun.*, 1993, 1002–1004, which also discloses o-methoxymethyl sordaricin methyl ester. The diacetate of 4-deformyl-4-hydroxymethyl sordaricin is disclosed in Mander and Robinson, *J. Org. Chem.*, 1991, 56(11): 3395–3601. Neither sordaricin nor the reported derivatives thereof has been shown to have biological activity.

Balkovec et al. (U.S. Pat. Nos. 6,040,463 and 6,136,853) discloses a compound of sordarin derivative.

Nielsen-Kahn et al. (U.S. Pat. No. 5,972,996) and Tse, Bruno (U.S. Pat. No. 5,965,612) disclose a compound of 4-cyano-4-deformylsordarin derivatives.

Sturr et al. (U.S. Pat. No. 6,228,622) discloses a compound of C11-hydroxysodarin and a process for producing it using *Actinomyces* spp, (Merck Culture Collection MA7235) by a biotransformation.

An objective of the present invention is to provide a novel class of sordarin analogues derived from C-11-hydroxysordarin that are potent antifungal agents for general use and against pathogens associated with human and agricultural fungal infections.

SUMMARY OF THE INVENTION

The present invention relates to a novel compound of sordarin analogues derived from C-11-hydroxysordarin. These novel compounds are potent antifungal agents with a broad spectrum of activity, which can be used against pathogens associated with human and agricultural fungal infections. The present invention also include a method for preparing sordarin analogues, a pharmaceutical and agricultural composition containing the compounds, a method of treatment or prevention of a fungal infection in humans and animal, and a method of controlling fungal infections in humans, animals and plant materials using such compounds.

The present invention is directed to a compound of formula I:

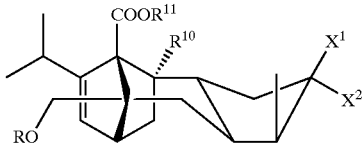

or a pharmaceutically or agriculturally acceptable salt thereof, wherein,

R is:
(a) hydrogen,
(b) $C(O)OR^1$,
(c) $C(O)NR^2R^3$,
(d) $C(O)R^4$,
(e) $CH(R^2)OR^5$,
(f) $C(R^6)(R^7)(R^8)$,
(g)

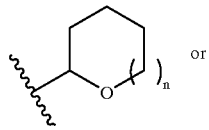

(h)

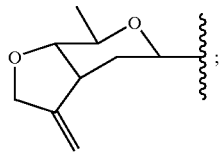

$R^1$ is:
(a) $(C_1–C_{14})$alkyl,
(b) $(C_2–C_{14})$alkenyl,
(c) $(C_2–C_{14})$alkynyl,
(d) $(C_3–C_{20})$cycloalkyl,
(e) aryl or
(f) aryl-$(C_1–C_6)$alkyl;

$R^2$ and $R^3$ are independently:
(a) H or
(b) $R^1$;

$R^4$ is:
(a) H,
(b) $R^1$ or
(c) $(CH_2)_mNR^2R^3$;

$R^5$ is:
(a) $R^1$ or
(b) $(CH_2)_xO(CH_2)_yH$;

$R^6$ is:
(a) H,
(b) $(C_1–C_{14})$alkyl,
(c) aryl,
(d) aryl-$(C_1–C_6)$alkyl,
(e) $(CH_2)_yCHR^9(CH_2)_zH$,
(f) $(CH_2)_yC≡C(CH_2)_zH$,
(g) $(CH_2)_yC(R^7)=CH(CH_2)_zH$, (h) $(CH_2)_yC{\equiv}C(CH_2)_mR^9$ or
(i) $(CH_2)_yC(R^7){=}CH(CH_2)_mR^9$;

$R^7$ and $R^8$ are independently:
  (a) H or
  (b) $(C_1-C_{14})$alkyl;

$R^9$ is:
  (a) OH or
  (b) $NR^2R^3$;

$R^{10}$ is:
  (a) C(O)H or
  (b) CN;

$R^{11}$ is:
  (a) H,
  (b) —$CH_2CH{=}CH_2$,
  (c)

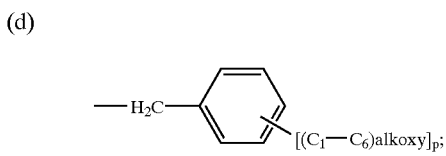
  [$(C_1-C_6)$alkyl]$_p$ or (d)

—$H_2C$— [$(C_1-C_6)$alkoxy]$_p$;

$X^1$ and $X^2$ are independently:
  (a) H, wherein $X^1$ and $X^2$ are not H simultaneously,
  (b) $(C_1-C_6)$alkyl,
  (c) $(C_1-C_6)$alkoxy,
  (d) $(C_2-C_6)$alkenyl optionally substituted with $R^1$,
  (e) OH, wherein $X^1$ and $X^2$ are not OH simultaneously,
  (f) OC[$(C_1-C_6)$alkyl]$_3$,
  (g) OC(O)$(C_1-C_6)$alkyl,
  (h) halo, wherein halo is F, Cl, Br or I,
  (i) SC(O)$(C_1-C_6)$alkyl,
  (j) S$(C_1-C_6)$alkyl,
  (k) SH,
  (l) $N_3$,
  (m) N[$(C_1-C_6)$alkyl]$_2$,
  (n) N[$(C_1-C_6)$alkyl]C(O)$(C_1-C_6)$alkyl or
  (o) CN; and
wherein $X^1$ and $X^2$ together can be oxo or $={CH_2}$;
n is: 0 or 1;
m is: 1–6;
p is: 0–5;
x is: 2–6;
y is: 0–6; and
z is: 0–6.

DETAILED DESCRIPTION OF THE INVENTION

The present invention is directed to a compound of sordarin analogues derived from C-11-hydroxysordarin, which is a potent antifungal agent with a broad spectrum of activity to treat a diseases associated with human and agricultural fungal infections.

The present invention is directed to a compound of formula I:

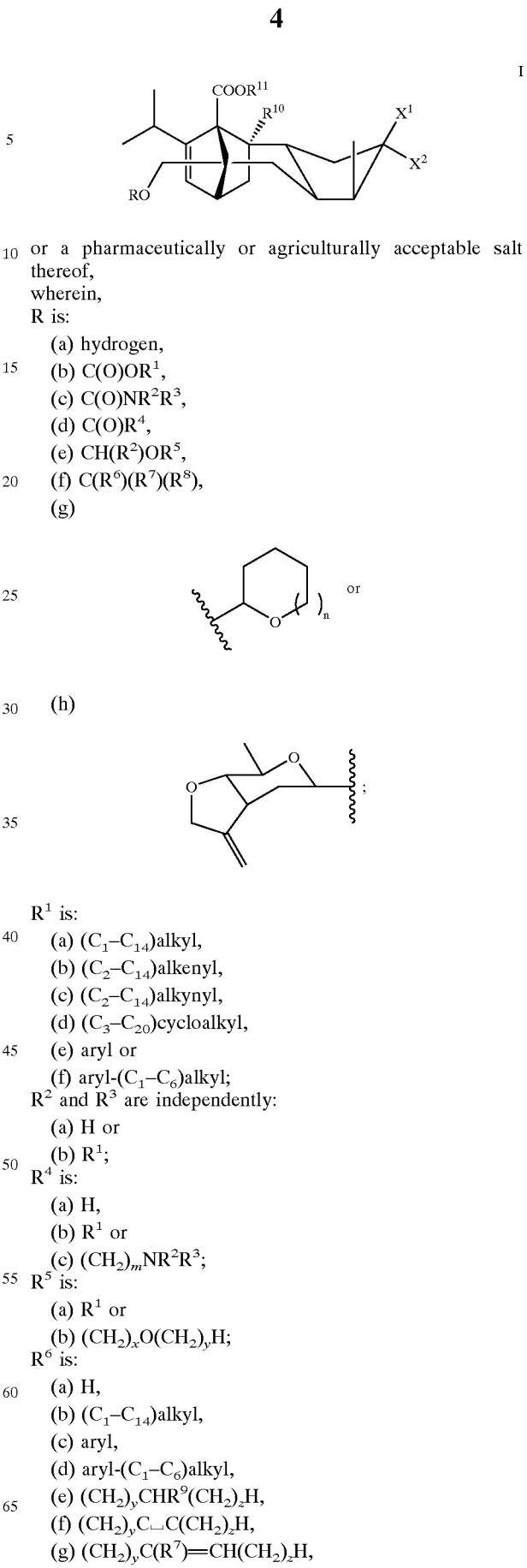

or a pharmaceutically or agriculturally acceptable salt thereof,
wherein,
R is:
  (a) hydrogen,
  (b) C(O)$OR^1$,
  (c) C(O)$NR^2R^3$,
  (d) C(O)$R^4$,
  (e) CH($R^2$)$OR^5$,
  (f) C($R^6$)($R^7$)($R^8$),
  (g)

or (h)

$R^1$ is:
  (a) $(C_1-C_{14})$alkyl,
  (b) $(C_2-C_{14})$alkenyl,
  (c) $(C_2-C_{14})$alkynyl,
  (d) $(C_3-C_{20})$cycloalkyl,
  (e) aryl or
  (f) aryl-$(C_1-C_6)$alkyl;

$R^2$ and $R^3$ are independently:
  (a) H or
  (b) $R^1$;

$R^4$ is:
  (a) H,
  (b) $R^1$ or
  (c) $(CH_2)_mNR^2R^3$;

$R^5$ is:
  (a) $R^1$ or
  (b) $(CH_2)_xO(CH_2)_yH$;

$R^6$ is:
  (a) H,
  (b) $(C_1-C_{14})$alkyl,
  (c) aryl,
  (d) aryl-$(C_1-C_6)$alkyl,
  (e) $(CH_2)_yCHR^9(CH_2)_zH$,
  (f) $(CH_2)_yC{\equiv}C(CH_2)_zH$,
  (g) $(CH_2)_yC(R^7){=}CH(CH_2)_zH$, (h) $(CH_2)_yC\equiv C(CH_2)_mR^9$ or (i) $(CH_2)_yC(R^7)=CH(CH_2)_mR^9$;

$R^7$ and $R^8$ are independently:

(a) H or (b) $(C_1-C_{14})$alkyl;

$R^9$ is:

(a) OH or (b) $NR^2R^3$;

$R^{10}$ is:

(a) C(O)H or (b) CN;

$R^{11}$ is:

(a) H, (b) —$CH_2CH=CH_2$, (c)

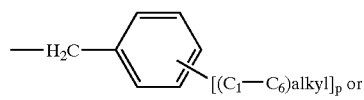

or (d)

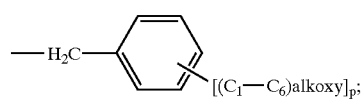

$X^1$ and $X^2$ are independently:

(a) H, wherein $X^1$ and $X^2$ are not H simultaneously, (b) $(C_1-C_6)$alkyl, (c) $(C_1-C_6)$alkoxy, (d) $(C_2-C_6)$alkenyl optionally substituted with $R^1$, (e) OH, wherein $X^1$ and $X^2$ are not OH simultaneously, (f) $OC[(C_1-C_6)alkyl]_3$, (g) $OC(O)(C_1-C_6)$alkyl, (h) halo, wherein halo is F, Cl, Br or I, (i) $SC(O)(C_1-C_6)$alkyl, (j) $S(C_1-C_6)$alkyl, (k) SH, (l) $N_3$, (m) $N[(C_1-C_6)alkyl]_2$, (n) $N[(C_1-C_6)alkyl]C(O)(C_1-C_6)$alkyl or (o) CN; and wherein $X^1$ and $X^2$ together can be oxo or $=CH_2$;

n is: 0 or 1;

m is: 1–6;

p is: 0–5;

x is: 2–6;

y is: 0–6; and z is: 0–6.

A preferred embodiment of the present invention provides the compound of formula I, wherein R is: (a) hydrogen, (b) $C(O)OR^1$, (c) $C(O)NR^2R^3$, (d) $C(O)R^4$, (e) $CH(R^2)OR^5$, (f) $C(R^6)(R^7)(R^8)$, (g)

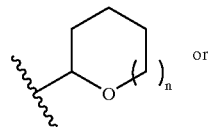

or (h)

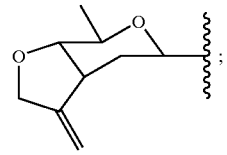

;

$R^{10}$ is: C(O)H; and $X^1$ and $X^2$ are independently:

(a) H, wherein $X^1$ and $X^2$ are not H simultaneously, (b) $(C_1-C_6)$alkyl, (c) $(C_1-C_6)$alkoxy, (d) $(C_2-C_6)$alkenyl optionally substituted with $R^1$, (e) OH, wherein $X^1$ and $X^2$ are not OH simultaneously, (f) $OC[(C_1-C_6)alkyl]_3$, (g) $OC(O)(C_1-C_6)$alkyl, (h) halo, wherein halo is F, Cl, Br or I, (i) $SC(O)(C_1-C_6)$alkyl, (j) $S(C_1-C_6)$alkyl, (k) SH, (l) $N_3$, (m) $N[(C_1-C_6)alkyl]_2$, (n) $N[(C_1-C_6)alkyl]C(O)(C_1-C_6)$alkyl or (o) CN; and wherein $X^1$ and $X^2$ together can be oxo or $=CH_2$.

Another preferred embodiment of the present invention provides the compound of formula I, wherein R is: (a) hydrogen, (b) $C(O)OR^1$, (c) $C(O)NR^2R^3$, (d) $C(O)R^4$, (e) $CH(R^2)OR^5$, (f) $C(R^6)(R^7)(R^8)$, (g)

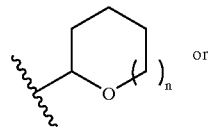

or (h)

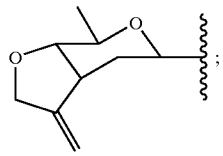

$R^{10}$ is: C(O)H;
$R^1$ is: H; and
$X^1$ and $X^2$ are independently H or halo, wherein either $X^1$ or $X^2$ is halo.

Yet another preferred embodiment of the present invention provides the compound of formula I, wherein
R is: C(O)OR$^1$;
$R^{10}$ is: C(O)H;
$R^{11}$ is: H; and
$X^1$ and $X^2$ are independently H or OH, wherein either $X^1$ or $X^2$ is OH.

Yet another preferred embodiment of the present invention provides the compound of formula I, wherein
R is C(O)NR$^2$R$^3$;
$R^{10}$ is C(O)H;
$R^{11}$ is H; and
$X^1$ and $X^2$ are independently H or OH, wherein either $X^1$ or $X^2$ is OH.

Yet another preferred embodiment of the present invention provides the compound of formula I, wherein
R is: C(O)R$^4$;
$R^{10}$ is: C(O)H;
$R^{11}$ is: H; and
$X^1$ and $X^2$ are independently H or OH, wherein either $X^1$ or $X^2$ is OH.

Yet another preferred embodiment of the present invention provides the compound of formula I, wherein
R is: C(R$^2$)OR$^5$;
$R^{10}$ is: C(O)H;
$R^1$ is: H; and
$X^1$ and $X^2$ are independently H or OH, wherein either $X^1$ or $X^2$ is OH.

Yet another preferred embodiment of the present invention provides the compound of formula I, wherein
R is: C(R$^6$)(R$^7$)(R$^8$);
$R^{10}$ is: C(O)H;
$R^{11}$ is: H; and
$X^1$ and $X^2$ are independently H or OH, wherein either $X^1$ or $X^2$ is OH.

Yet another preferred embodiment of the present invention provides the compound of formula I, wherein
R is

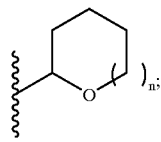

$R^{10}$ is C(O)H;
$R^{11}$ is H; and
$X^1$ and $X^2$ are independently H or OH, wherein either $X^1$ or $X^2$ is OH.

Yet another preferred embodiment of the present invention provides the compound of formula I, wherein
R is

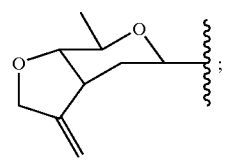

$R^{10}$ is C(O)H;
$R^{11}$ is H; and
$X^1$ and $X^2$ are independently H or OH, wherein either $X^1$ or $X^2$ is OH.

Yet another preferred embodiment of the present invention provides the compound of formula I, wherein
R is

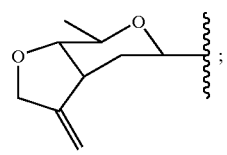

$R^{10}$ is C(O)H;
$R^{11}$ is H; and
$X^1$ and $X^2$ are independently H or Cl, wherein either $X^1$ or $X^2$ is Cl.

Yet another preferred embodiment of the present invention provides the compound of formula I, wherein
R is: CH(R$^6$)(R$^7$);
$R^{10}$ is: C(O)H;
$R^{11}$ is: H;
$R^6$ is: (a) H,
  (b) (C$_1$–C$_{14}$)alkyl,
  (c) aryl,
  (d) aryl-(C$_1$–C$_6$)alkyl,
  (e) (CH$_2$)$_y$CH(OH)(CH$_2$)$_z$H or
  (f) (CH$_2$)$_y$C(R$^7$)=CH(CH$_2$)$_z$H;
$R^7$ is: H or (C$_1$–C$_{14}$)alkyl; and
$X^1$ and $X^2$ are independently H or OH, wherein either $X^1$ or $X^2$ is OH.

Yet another preferred embodiment of the present invention provides the compound of formula I, wherein
$R^{10}$ is: C(O)H;
$R^{11}$ is: H;
R is: (a) (C$_1$–C$_7$)alkyl,
  (b) aryl-(C$_1$–C$_6$)alkyl,
  (c) (CH$_2$)$_y$CH=CH(CH$_2$)$_z$H,
  (d) [(C$_1$–C$_6$)alkyl]—CH$_2$CH=CHCH$_2$CH$_3$ or
  (e) [(C$_1$–C$_6$)alkyl]—CH$_2$CH=CH(CH$_2$)$_2$CH$_3$; and
$X^1$ and $X^2$ are independently H or OH, wherein either $X^1$ or $X^2$ is OH.

Yet another preferred embodiment of the present invention provides the compounds as shown in the table below:

| | |
|---|---|
| (1S,3aR,4S,8aS)-6-(acetyloxy)-8a-[(acetyloxy)methyl]-4-formyl-3-isopropyl-7-methyl-4,4a,5,6,7,7a,8,8a-octahydro-1,4-methano-s-indacene-3a(1H)-carboxylic acid | 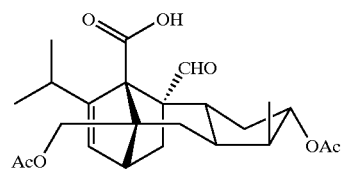 |
| (1S,3aR,4S,8aS)-6-(methoxy)-8a-[(methoxy)methyl]-4-formyl-3-isopropyl-7-methyl-4,4a,5,6,7,7a,8,8a-octahydro-1,4-methano-s-indacene-3a(1H)-carboxylic acid | 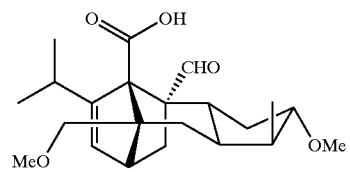 |
| (1S,3aR,4S,8aS)-6-(propoxy)-8a-[(propoxy)methyl]-4-formyl-3-isopropyl-7-methyl-4,4a,5,6,7,7a,8,8a-octahydro-1,4-methano-s-indacene-3a(1H)-carboxylic acid | 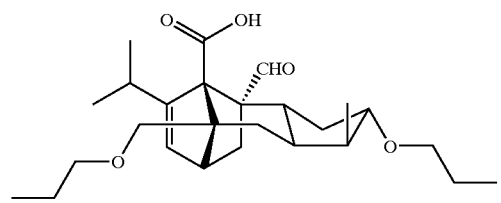 |
| (1R,3aR,4S,8aS)-6-(butoxymethyl)-4-formyl-6-hydroxy-3-isopropyl-7-methyl-4,4a,5,6,7,7a,8,8a-octahydro-4,4-methano-s-indacene-3a(1H)-carboxylic acid | 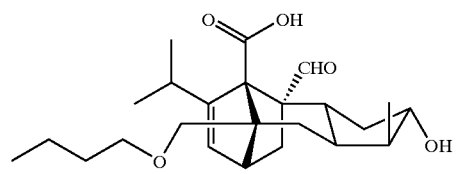 |
| (1R,3aR,4S,8aS)-8a-(butoxymethyl)-6-chloro-4-formyl-3-isopropyl-7-methyl-4,4a,5,6,7,7a,8,8a-octahydro-1,4-methano-s-indacene-3a(1H)-carboxylic acid | 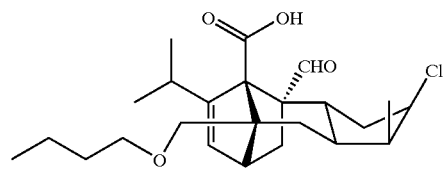 |
| (1R,3aR,4S,8aS)-8a-(butoxymethyl)-6-azido-4-formyl-3-isopropyl-7-methyl-4,4a,5,6,7,7a,8,8a-octahydro-1,4-methano-s-indacene-3a(1H)-carboxylic acid | 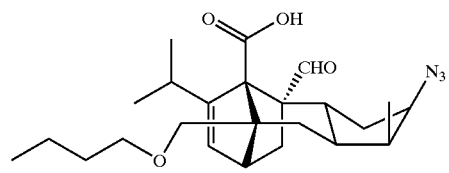 |
| (1R,3aR,4S,8aS)-8a-(butoxymethyl)-4-formyl-6-hydroxy-3-isopropyl-7-methyl-4,4a,5,6,7,7a,8,8a-octahydro-1,4-methano-s-indacene-3a(1H)-carboxylic acid | 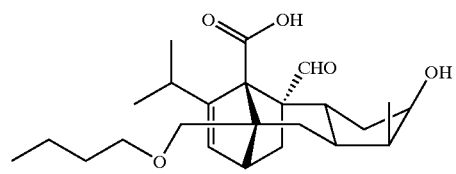 |
| (1R,3aR,4S,8aS)-8a-(butoxymethyl)-4-formyl-3-isopropyl-6-methoxy-7-methyl-4,4a,5,6,7,7a,8,8a-octahydro-1,4-methano-s-indacene-3a(1H)-carboxylic acid | 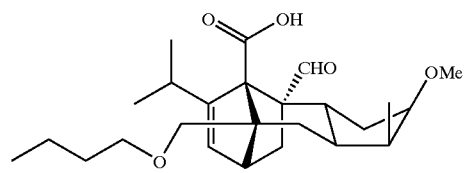 |

| | |
|---|---|
| (1R,3aR,4S,8aS)-8a-(butoxymethyl)-6-fluoro-4-formyl-3-isopropyl-7-methyl-4,4a,5,6,7,7a,8,8a-octahydro-1,4-methano-s-indacene-3a(1H)-carboxylic acid | 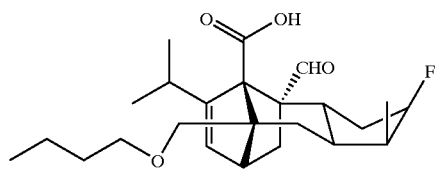 |
| (1R,3aR,4S,8aS)-8a-(butoxymethyl)-6-cyano-4-formyl-3-isopropyl-7-methyl-4,4a,5,6,7,7a,8,8a-octahydro-1,4-methano-s-indacene-3a(1H)-carboxylic acid | 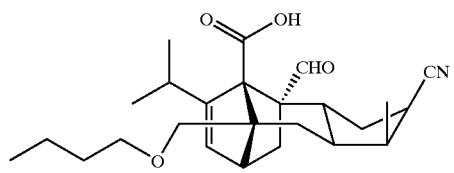 |
| (1R,3aR,4S,8aS)-8a-(hydroxymethyl)-4-formyl-3-isopropyl-6-chloro-7-methyl-4,4a,5,6,7,7a,8,8a-octahydro-1,4-methano-s-indacene-3a(1H)-carboxylic acid | 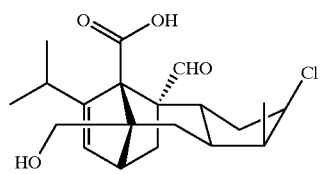 |
| (1R,3aR,4S,8aS)-6-chloro-4-formyl-3-isopropyl-7-methyl-8a-{[(7-methyl-3-methylenehexahydro-2H-furo[2,3-c]pyran-5-yl)oxy]methyl}-4,4a,5,6,7,7a,8,8a-octahydro-1,4-methano-s-indacene-3a(1H)-carboxylic acid | 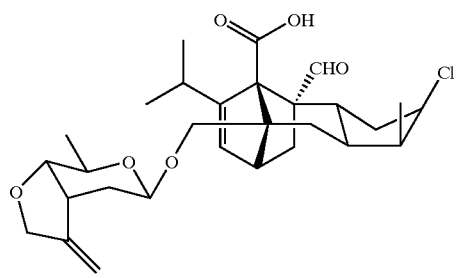 |

Another aspect of the present invention provides a pharmaceutical composition, which comprises a compound of formula I and a pharmaceutically acceptable carrier.

Yet another aspect of the present invention provides a pharmaceutical formulation comprising a combination of a compound of formula I and a second therapeutic agent or its pharmaceutically acceptable salt. The second therapeutic agent is a compound selected from the group consisting of an azole, polyene, purin uncleotide inhibitor, pneumocandin derivative, echinocandin derivative, the elongation factor inhibitor, and immunomodulating agent. A preferred second therapeutic agent is a compound selected from the group consisting of intraconazole, flucytosine, fluconazole, and amphotericin B.

Yet another aspect of the present invention provides an agrochemical composition, which comprises a compound of formula I and an agriculturally acceptable carrier.

Yet another aspect of the present invention provides an agrochemical composition, which comprises a compound of formula I and a second active ingredient selected from the group consisting of herbicides, insecticides, bactericides, nematocides, molluscicides, growth regulators, micronutrients, fertilizers, and fungicides.

Yet another aspect of the present invention provides a method for the treatment or prevention of a fungal infection in a mammal (including humans), which comprises administering to said mammal therapeutically effective amounts of a compound of formula I.

Yet another aspect of the present invention provides a method for the treatment or prevention of fungal infection in a mammal, which comprises administering to said mammal therapeutically effective amounts of a compound of formula I and a second therapeutic agent selected from the group consisting of an azole, polyene, purin nucleotide inhibitor, pneumocandin derivative, echinocandin derivative, elongation factor inhibitor, and immunomodulating agent.

Yet another aspect of the present invention provides a method for controlling phytopathogenic fungi, which comprises administering to a plant in need of such control therapeutically effective amounts of a compound of formula I.

A further aspect of the present invention provides a method for controlling phytopathogenic fungi, which comprises administering to a plant in need of such control therapeutically effective amounts of a compound of formula I and a second active ingredient selected from the group consisting of herbicides, insecticides, bactericides, nematocides, molluscicides, growth regulators, micronutrients, fertilizers, and fungicides.

As used herein, unless otherwise specified, the following terms have the indicated meanings.

The term "alkyl", alone or as part of a group (e.g. aryl-alkyl), means a straight or branched chain alkyl moiety, optionally substituted with cycloalkyl or cycloalkenyl, having the designated number of carbon atoms such as methyl, ethyl, n-propyl, n-butyl, isopropyl, isobutyl, isopentyl, s-butyl, t-butyl, n-hexyl, n-octyl, decyl, undecyl, cyclopropylmethyl, cyclobutylmethyl, 2-cyclopentylethyl, cyclododecylmethyl, cyclohexylmethyl and the like.

The term "cycloalkyl" means a saturated carbocycle containing one or more rings of from 3 to 12 carbon atoms, optionally substituted with $C_{1-3}$ alkyl. Examples of cycloalkyl groups are cyclopropyl, cyclobutyl, cyclopentyl, cyclohexyl, methylcyclohexyl, cycloheptyl, adamantyl, 2-ethyl-1-bicyclo[4.4.0]decyl, and the like.

The term "aryl", alone or as part of a group (e.g. arylalkyl), includes phenyl, biphenyl, terphenyl, naphthyl, anthracenyl or heteroaryl each optionally substituted by one to three groups independently selected from halogen, hydroxyl, carboxyl, $C_{1-6}$ alkyl, $C_{1-6}$ alkoxy or $C_{1-4}$ alkoxycarbonyl. The heteroaryl group may be a 5- or 6-membered heteroaromatic ring containing one to three heteroatoms selected from nitrogen, oxygen and/or sulfur. Examples of heteroaryl groups include, but are not limited to: pyridyl, quinolinyl, furyl, thienyl and pyrrolyl.

The term "alkenyl" means a straight or branched carbon chain having at least one carbon-carbon double bond. Examples include vinyl, allyl, butenyl, isobutenyl, butadienyl, and the like.

The term "cycloalkenyl" means an unsaturated carbocycle containing one or more rings of from 3 to 12 carbon atoms, optionally substituted with $C_{1-3}$ alkyl. Examples of cycloalkenyl groups are cyclobutenyl, cyclopentenyl, cyclohexenyl, methylcyclohexenyl, and the like.

The term "alkynyl" means a straight or branched carbon chain having at least one carbon-carbon triple bond. Examples include acetylenyl, propargyl, butynyl, 1,3-pentadiynyl, and the like.

The term "controlling", used in association with phytopathogenic fungi, includes prophylactic use (i.e. to protect against infection) and curative use (i.e. to eradicate infection).

The term "plants" include live plants, foliage, flowers, seeds, fruits, and other materials derived from plants. The term also includes roots of the plant via application of the active ingredient to the soil.

The term "composition", as in pharmaceutical or agricultural composition, is intended to encompass a product comprising the active ingredient(s), and the inert ingredient(s) that make up the carrier, as well as any product which results, directly or indirectly, from combination, complexation, aggregation or other interactions of any two or more of the active ingredient(s) and/or the inert ingredient(s) or from dissociation of one or more of the active ingredient(s) and/or the inert ingredient(s), or from other types of reactions of one or more of the active ingredient(s) and/or the inert ingredient(s).

Suitable salts of a compound of formula I include inorganic base salts such as alkali metal salt (e.g. sodium and potassium salts), ammonium salts, and organic base salts. Suitable organic base salts include amine salts such as tetraalkylammonium (e.g. tetrabutylammonium or trimethylcetylammonium), trialkylamine (e.g. triethylamine), dialkylamine salts (e.g. dicyclohexylamine), optionally substituted benzylamine (e.g. phenylbenzylamine or parabromobenzylamine), ethanolamine, diethanolamine, N-methylglucosamine, N-methylpiperidine, pyridine and substituted pyridine (e.g. collidine, lutidine, 4-dimethylaminopyridine), and tri(hydroxymethyl)methylamine salts, and amino acid salts (e.g. lysine or arginine salts).

A mammal as used in here includes a human and a warm blooded animal such as a cat, a dog and the like.

The present invention of sordarin analogues of formula I are prepared from C11-hydroxysordarin as shown below, which is described in U.S. Pat. No. 6,228,622 B1.

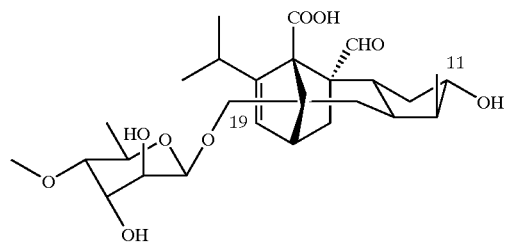

C-11-hydroxysordarin

As disclosed in U.S. Pat. No. 6,228,622 B1, C-11-hydroxysordarin is prepared by a process of biotransformation of sordarin (II). The process involves a fermentation of the microorganism *Actinomyces* spp. MA7325, ATCC No. 202103 in the presence of the substrate compound, sordarin of the formula given below under appropriate conditions in an aqueous nutrient medium containing sources of assimilable carbon and nitrogen.

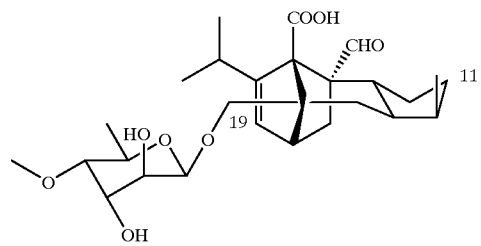

Sordarin (II)

A sample of the microorganism *Actinomyces* spp. has been deposited under the Budapest Treaty in the culture collection of the American Type Culture Collection, 10801 University Boulevard, Manassas, Va., 20110-2209, on Apr. 1, 1998 and assigned accession number ATCC 202103.

MA7235 can be generally described as follows. Observations of growth, and general cultural characteristics were made in accordance with the methods of Shirling and Gottleib (International J. System. Bacteriol. 16:313–340). Chemical composition of the cells was determined using the methods of Lechevalier and Lechevalier (in Actinomycete Taxonomy, A. Dietz and D. W. Thayer, Ed. Society for Industrial Microbiology, 1980). Whole Cell Fatty Acids were derivatrized and analyzed as methyl esthers (Fames) by Gas Chromatography by the procedure of Miller and Berger using as MIDI Microbial Identification system (Microbial Identification Systems, Newark, Del.). Coloration of the culture was determined by comparison with color standards in the Munsell color charts (Macbeth Division of Kollmorgen Instruments Corp. P.O. Box 230 Newburgh, N.Y. 12551-0230).

The compounds of the present invention (the compounds of formula I) are prepared by the following reaction schemes and examples. The conditions are representative and are not meant to be limiting.

REACTION SCHEME 1

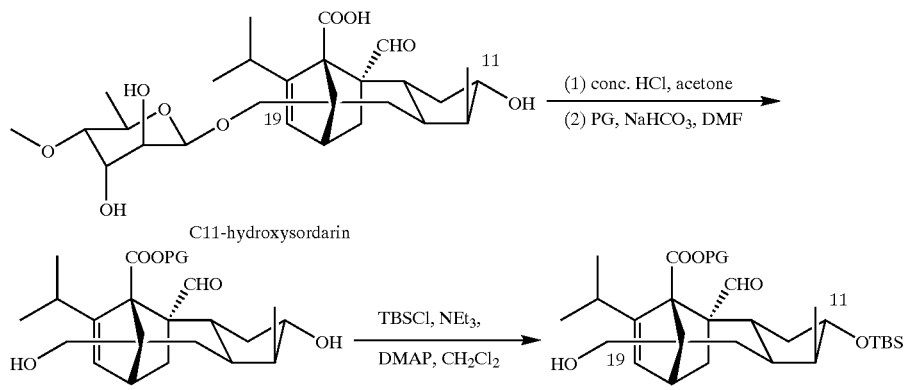

PG is a carboxylic acid protecting group.
DMAP is 4-dimethylaminopyridine.

Reaction Scheme 1 shows the hydrolysis of C-11-hydroxysordarin to generate the aglycone. The aglycone can be prepared by treating C-11-hydroxysordarin with hydrochloric acid in a polar solvent such as acetone. The carboxyl group is first protected with a suitable protecting group, such as $-CH_2C_6H_4(OCH_3)$ or $-CH_2OC(O)C(CH_3)_3$ and then the hydroxyl group at C-11 are protected with the same or an alternate suitable protecting group. Selective protection at C-11, as its TBS (tert-butyldimethylsilyl) ether, allows the formation of derivatives at C-19 position as illustrated in the following Reaction Schemes 2–5.

REACTION SCHEME 2

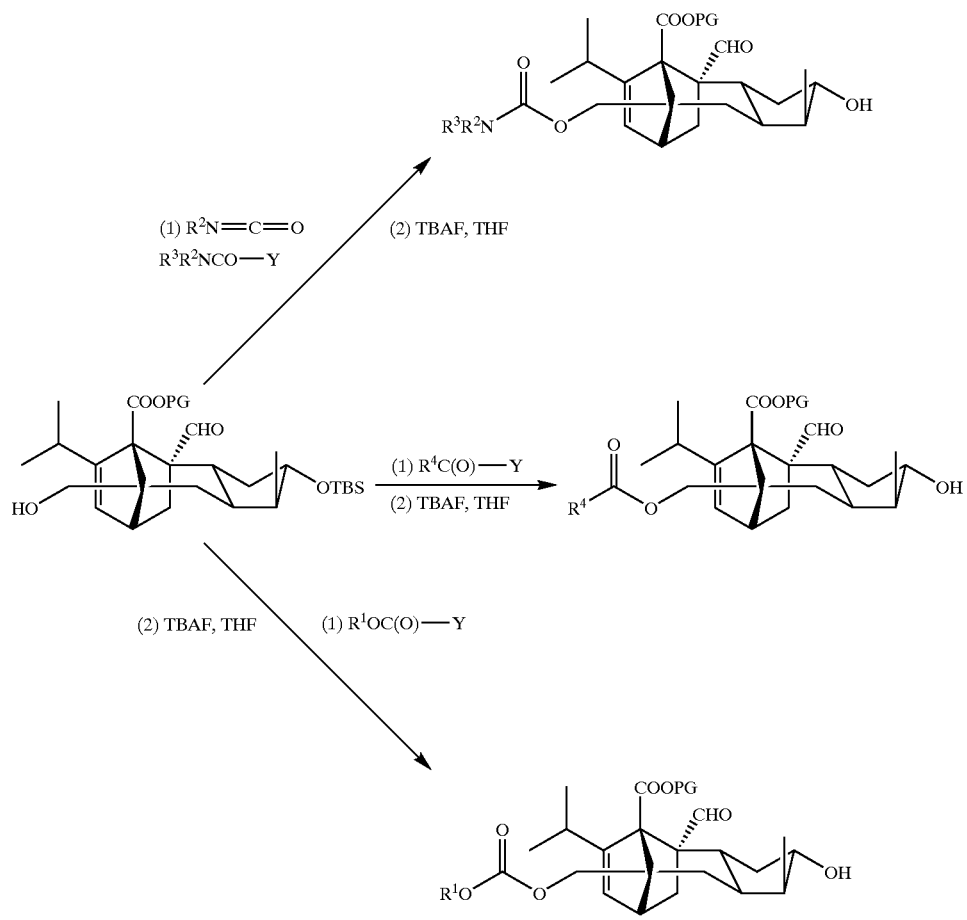

PG is a carboxylic acid protecting group;
C(O)—Y is an activated carbonyl such as a acid chloride or an anhydride;
TBAF is tetrabutylammonium fluoride.

Reaction Scheme 2 illustrates the synthesis of carbamate, ester and carbonate derivatives of sordarin aglycone. The preparation of carbamates may be carried out by treatment of suitably protected sordarin aglycone with an isocyanate (in the examples where $R^3$ is H) or a carbamoyl halide or other activated carbamoylating agent in an inert solvent. Removal of the protecting group produces a carbamate compound of formula I.

Ester derivatives may be prepared in a similar fashion by treatment of protected sordarin aglycone with an activated carbonyl compound such as an acid chloride or mixed anhydride preferably in the presence of an acylation catalyst such as N,N-dimethylaminopyridine and a base such as pyridine. Removal of the protecting group yields an ester compound of formula I.

Carbonate derivatives may be prepared by the treatment of protected sordarin aglycone with an activated carbonate such as a chloroformate or pyrocarbonate. An acylation catalyst such as N,N-dimethylaminopyridine and a base such as pyridine is preferably employed in the reaction mixture. Removal of the protecting group yields a carbonate compound of formula I.

Reaction Scheme 3 shows the synthesis of ether derivatives of sordarin aglycone. Treatment of the carboxylic acid-protected aglycone with an α-haloether under basic conditions or a vinyl ether under acidic conditions produce the substituted α-alkoxyether derivatives. Treatment of protected sordarin aglycone with a primary or secondary halide or sulfonate and a suitable base such as sodium hydride under $S_N2$ reaction conditions gives the corresponding primary or secondary ether derivatives, whereas treatment of the aglycone with a tertiary alcohol, halide or sulfonate and a Lewis acid under $S_N1$ conditions afford the corresponding tertiary ether derivative. Removal of the protecting group from the compound give a compound of formula I.

REACTION SCHEME 4

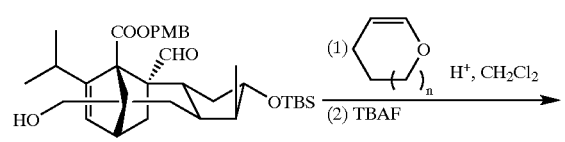

REACTION SCHEME 3

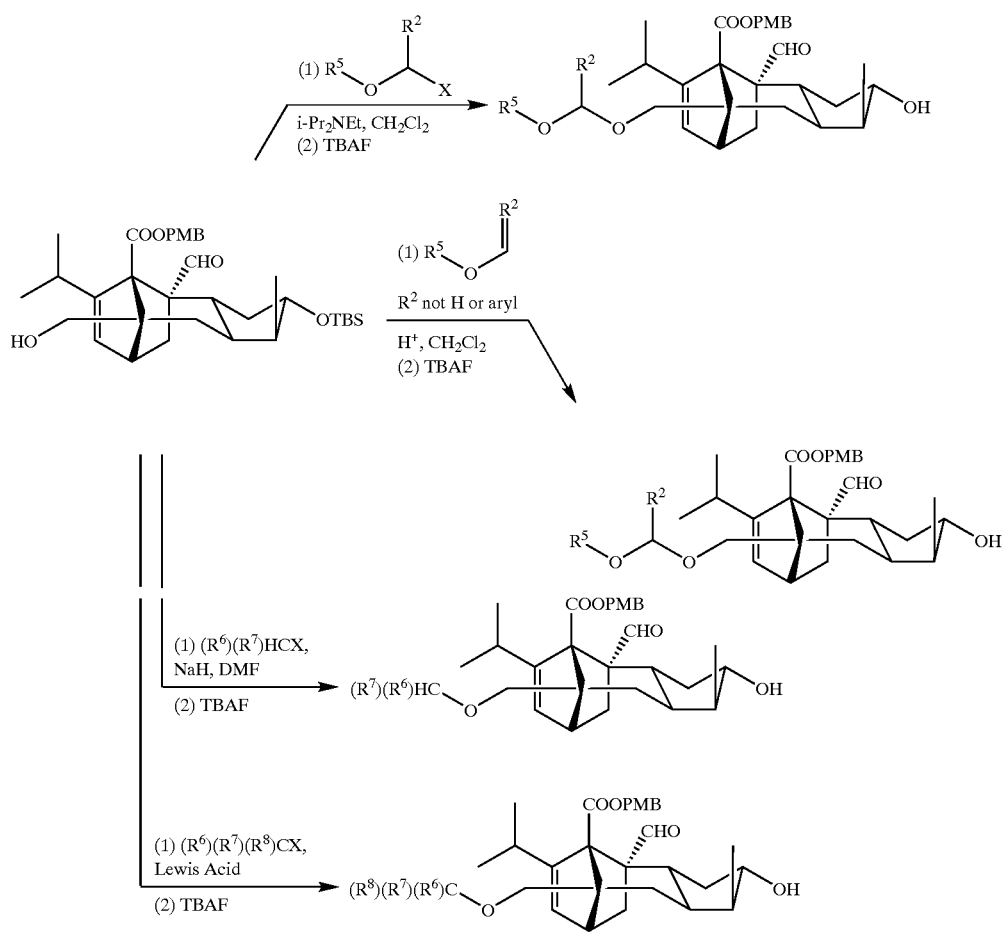

PG is a carboxylic acid protecting group;
X is a conventional leaving group such as halide or sulfonate.

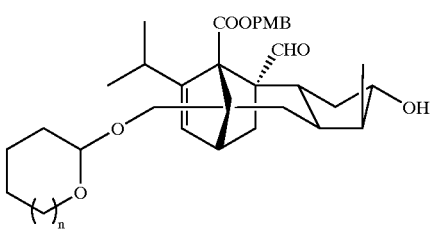

Reaction Scheme 4 shows the preparation of cyclic acetals from protected sordarin aglycone. Treatment of the aglycone with a cyclic vinyl ether in the presence of an acid catalyst followed by removal of the protecting group gives a compound of formula I.

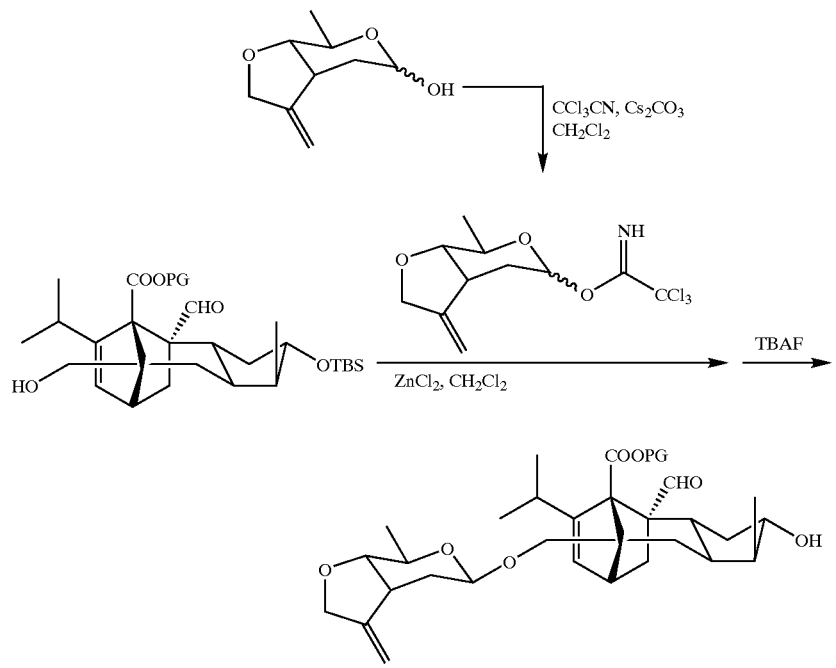

Reaction Scheme 5 provides an additional method of derivation at C-19 via the reaction with an activated sugar unit such as its imidate in the presence of Lewis acid such as $ZnCl_2$ to generate a new sugar. This C-11-hydroxysordarin compound can be further reacted to give a compound containing a halo substituent, such as Cl, Br, I or F at C-11 position.

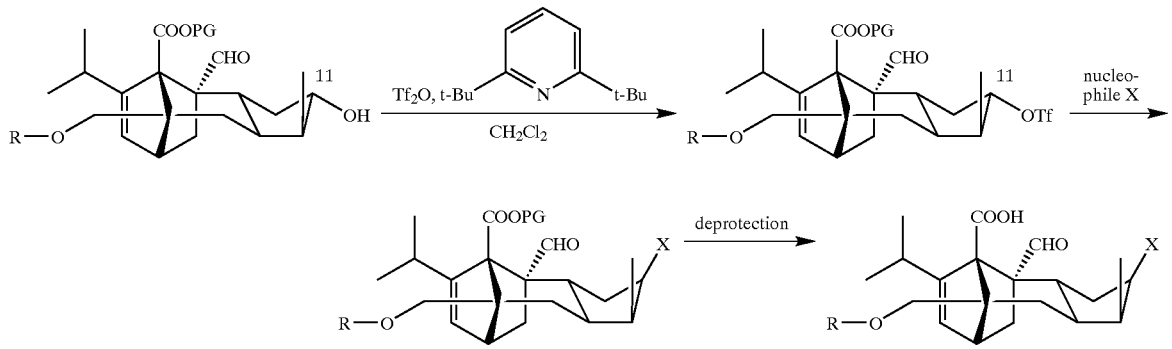

Reaction Scheme 6 provides the transformation at C-11 position through $S_N2$ reaction after removing the tert-butyldimethylsilyl (TBS) ether at C-11 to generate the free alcohol derivative of sordarin aglycone. The reaction involves the initial formation of a triflate from alcohol. The triflate is then displaced by various nucleophiles under $S_N2$ reaction conditions to yield the derivatives. Removal of the protecting group gives the final sordarin C-11 derivatives of a compound of formula I.

REACTION SCHEME 7

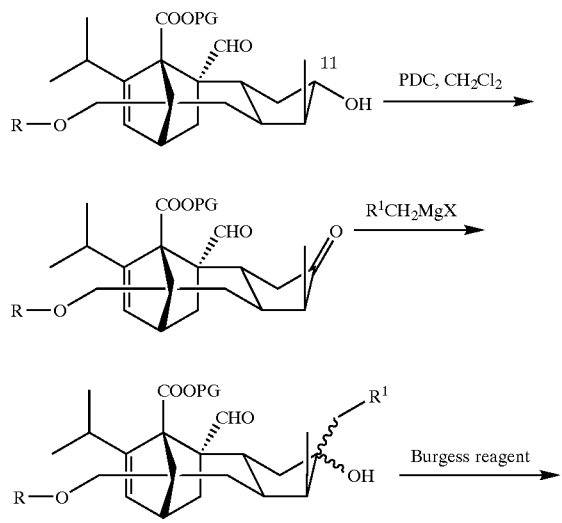

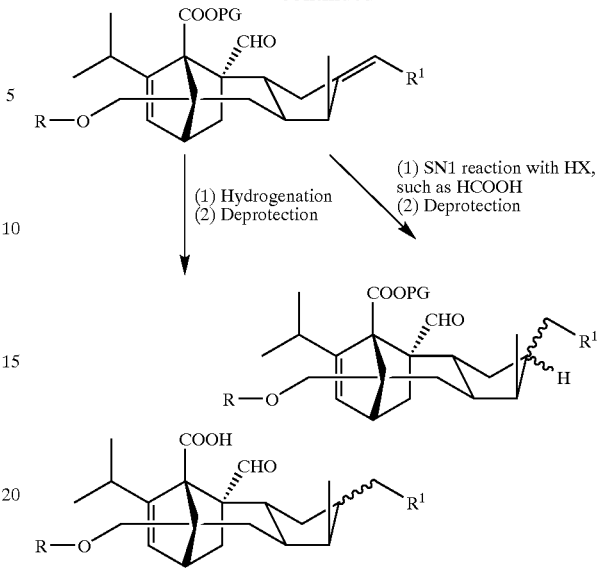

Reaction Scheme 7 shows the transformation at C-11 position through $S_N2$ reaction after removing tert-butyldimethylsilyl ether at C-11 to generate the free alcohol derivative of sordarin aglycone. The reaction involves the oxidation of the alcohol to the corresponding ketone. Subsequent reaction with a Grignard reagent, $R^1CH_2MgX$, followed by dehydration with Burgess' reagent [(methoxycarbonylsulfamoyl)-triethylammonium hydroxide inner salt] affords the exocyclic double bond. The alkene formed could be reduced under hydrogenation conditions to generate an alkyl derivative. Alternatively, the alkene could react under $S_N1$ reaction condition to afford another set of derivatives. Removal of the protecting group affords the final sordarin C-11 derivatives of a compound of formula I.

REACTION SCHEME 8

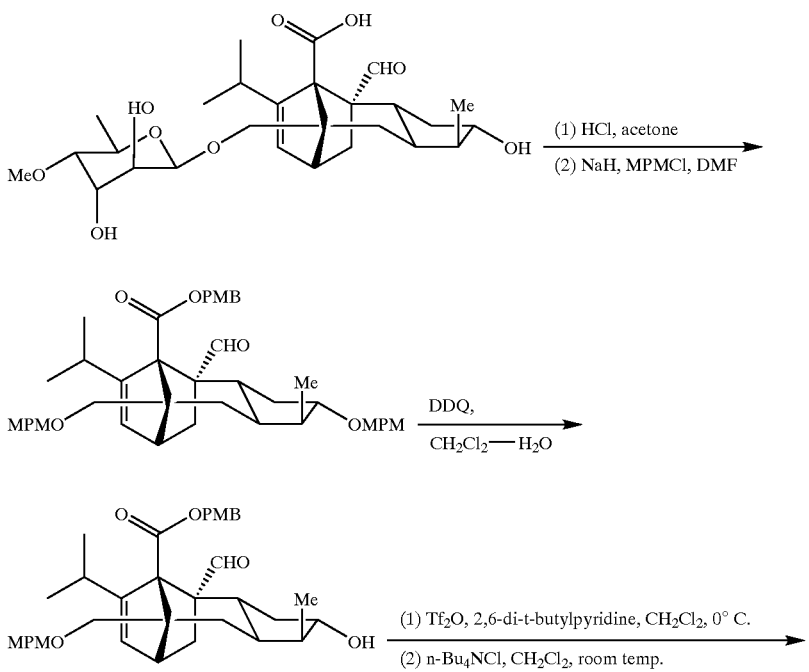

-continued
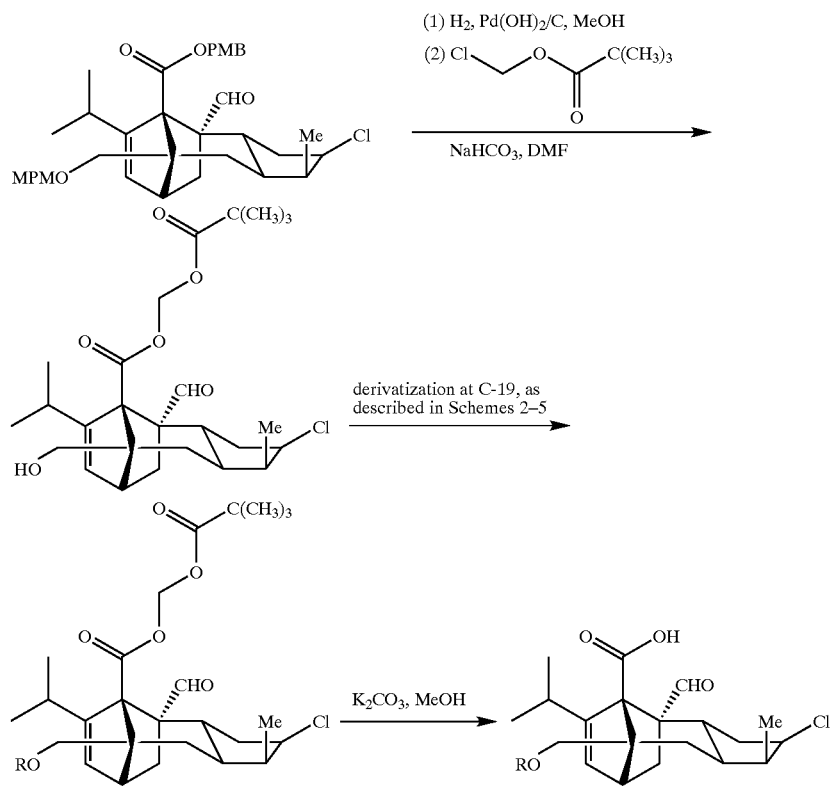
Reaction Scheme 8 provides another synthetic route to generate analogs at the C-11 position, which first modifies C-11 and then C-19 to produce a compound of formula (I).
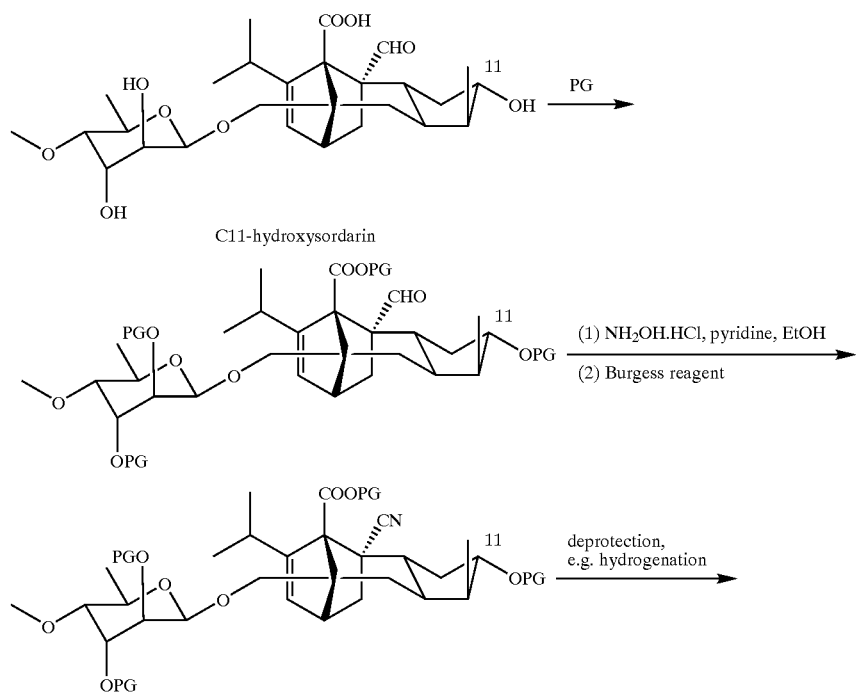

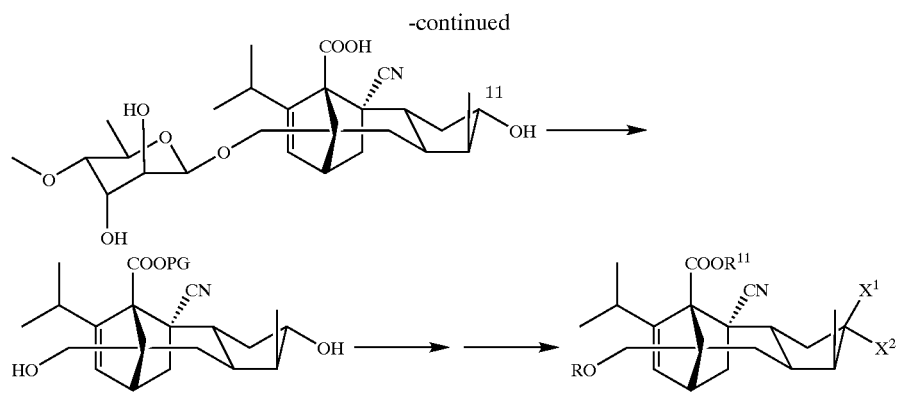

Reaction Scheme 9 shows the preparation of carboxy-protected 4-cyano-4-deformylsordarin having hydroxy group at C-11. The sordarin nitrile analogues can be formed in the same way as in the formation of sordarin aldehyde analogues, which are described in Reaction Schemes 1–8. The alcohols and the carboxylic acid are first globally protected as benzyl ethers or in other protected forms. The formyl group is transformed to the aldoxime, which is then dehydrated to the nitrile (cyano group) with a suitable agent such as Burgess's reagent, (methoxycarbonylsulfamoyl)-triethylammonium hydroxide inner salt. After a universal deprotection, the nitrile analog is formed, which is then undergoes transformation at C-11 or C-19 as shown in Reaction Schemes 1–8.

Utility

The compounds of formula I are antifungal agents useful as human and animal medicaments, as well as crop protectants.

Elongation factor 2 (EF2) is an essential protein catalyzing ribosomal translocation during protein synthesis in eukaryotic cells. It is highly conserved in all eukaryotes, and has been found to be largely interchangeable in in-vitro protein synthesis systems reconstituted from such divergent organisms as human, wheat germ and fungi. The sordarin compounds have been identified to be selective inhibitors of fungal protein synthesis via a selective interaction with fungal EF2, which can eradicate invading organisms while sparing the host of any detrimental effects.

The compounds of formula I are very active fungicides useful in combating fungal infections in animals, including humans. For example, they may be used in the treatment of fungal infections caused by organisms such as species of *Candida* (e.g. *Candida glabrata*, (*Torulopsis glabrata*), *Candida lusitaniae*, *Candida parapsilosis*, *Candida krusei*, *Candida guilliermondi*, *Candida tropicalis*, and *Candida pseudotropicalis*), *Cryptococcus neoformans*, *Pneumocystis carinii*, *Aspergillus* Sp (e.g. *Aspergillus flavus*, *Aspergillus fumigatus* and *Aspergillus nidulans*), *Coccidioides* (e.g. *Coccidioides immitis*), *Paracoccidioides* (e.g. *Paracoccidioides brasiliensis*), *Histoplasma* (e.g. *Histoplasma capsulatum*), *Blastomyces* (e.g. *Blastomyces dermatitidis*) or *Saccharomyces* (e.g. *Saccharomyces cerevisiae*). They may also be used to treat other fungal infections caused by species of *Trichophyton*, *Microsporum* or *Epidermophyton* (e.g. *Trichophyton mentographytes*, *Trichophyton rubrum*, *Microsporum canis* or *Epidermophyton floccosum*), or in mucosal infections caused by *Candida albicans*.

The compounds of formula I may also be used to treat other infections caused by species of filamentous fungi such as *Geotrichum* (e.g. *Geotrichum clavatum*), *Trichosporon* (e.g. *Trichosporon beigelii*), *Blastoschizomyces* (e.g. *Blastoschizomyces capitatus*), *Sporothrix* (e.g. *Sporothrix schenckii*), *Scedosporium* (e.g. *Scedosporium apiosperum*), *Cladosporium* (e.g. *Cladosporium carrionii*) and *Pityrosporum ovale*.

The compounds of formula I may also be used to treat infections caused by protozoa such as *Toxoplasma*, *Cryptosporidium*, *Leishmania*, *Tripanosoma*, *Giardia* and *Trichomonas*.

The in-vitro evaluation of the anti-fungal activity of compounds of the present invention is performed on liquid or solid medium by the anti-fungal two-fold serial dilution technique of determining the minimum inhibitory concentration (MIC) of anti-fungal agent that inhibited development of growth after 24 to 48 hours of incubation at 35° C. In practice, a series of agar plates or broth microdilution panels containing two-fold dilutions of anti-fungal agent tested are inoculated with a standard culture of a clinically relevant pathogen, for example, *Candida albicans*. The agar plates or broth microdilution panels are then examined for the presence or absence of growth of the fungus and the appropriate MIC values were noted. Visualization of endpoints is assisted by employment of the vital stain Alamar Blue.

The in-vitro assay evaluation of the antifungal activity of compounds of formula I to determine antifungal spectrum at the level of the EF2 target can also be carried out as described below:

Assay procedure: *S. cerevisiae* ribosomes and post-ribosomal supernatants are prepared from cultures of grown to mid-logarithmic phase in YPAD medium, which are washed twice with water and disrupted by shaking about two hours at about 4° C. with 0.5 mm glass beads in buffer containing 50 mM HEPES pH 7.5, 10% glycerol, 1 mM dithiothreitol and 1 mM EDTA. After centrifugation of the lysate at 100,000×G, the ribosomal pellet is washed three times by resuspension in 0.5M KCl, 20% sucrose and 10 mM MgCl2, and sedimentation at 100,000×G for about two hours. Ribosomes are then resuspended in the breakage buffer as described above plus 2 mM $MgCl_2$ and their concentration is determined by absorbance at 260 Å. The supernatant from the original 100,000×G sedimentation after breakage is desalted by passage through a Sephadex G10 column in the breakage buffer and protein is determined by Bradford assay. Both preparations are stored at about −70° C. without significant activity loss for up to a year. Post-ribosomal supernatants and ribosomes from pathogenic *Candida* are prepared the same way. In vitro incorporation is performed using 0.05$A_{260}$ of ribosomes, from *Saccharo-*

*myces cerevisiae, Candida* spp or *Aspergillus nidulans* and 3 µg of the corresponding S100 extract for each 12.5 µL assay. Incorporation is performed for about 10 minutes at about 22° C. in 12.5 µL volumes in microfuge tubes containing ribosomes and post-ribosomal supernatant as listed above, 3H-phenylalanine (400 dpm/pmol), 100 mM KCl, 33 mM HEPES pH 7.5, 14 mM $MgCl_2$, 400 nM ATP, 40 nM GTP, 16 mM creatine phosphate, 3 mM dithiothreitol, 0.5 mg/mL polyuridylic acid (Calbiochem) and 0.1 units creatine kinase (Sigma). After about 10 minutes incorporation, about 10 µL is spotted on a Whatman 3 mm filter disc numbered in pencil, and the disc is added to 10% trichloracetic acid (5 ml/filter). When all discs are added, the TCA is heated to about 80° C. for about 10 minutes, and discs is washed twice with ethanol and then dried for scintillation counting. Titration is performed by sordarin derivatives diluted in 10% DMSO and incorporation plotted as a function of concentration. $IC_{50}$ values are determined from plots of incorporation in presence of increasing amounts of inhibitor versus incorporation in the presence of no inhibitor.

The in-vivo evaluation of compounds of formula I can be carried out at a series of dose levels by administration (e.g. subcutaneously, orally, intraperitoneally or intravenously) to mice inoculated intravenously with a strain of *Candida* spp. The kidneys of the test animals may be removed and quantitated for viable *Candida* spp. and the reduction in infection may be determined relative to untreated control animals.

In view of their antifingal activity, compounds of formula I are useful for the treatment and/or prevention of a variety of fungal infections in human beings and animals. Such infections include superficial, cutaneous, subcutaneous and systemic mycotic infections such as respiratory tract infections, gastrointestinal tract infections, cardiovascular infections, urinary tract infections, CNS infections, candidiasis and chronic mucocandidiasis (e.g. thrush and vaginal candidiasis) and skin infections caused by fungi, cutaneous and mucocutaneous candidiasis, dermatophytoses including ringworm and tinea infections, athletes foot, paronychia, pityriasis versicolor, erythrasma, intertrigo, fungal diaper rash, candida vulvitis, candida balanitis and otitis externa. They may also be used as prophylactic agents to prevent systemic and topical fungal infections. Use as prophylactic agents may, for example, be appropriate as part of a selective gut decontamination regimen in the prevention of infection in immuno-compromised patients (e.g. AIDS patients, patients receiving cancer therapy or transplant patients). Prevention of fungal overgrowth during antibiotic treatment may also be desirable in some disease syndromes or iatrogenic states.

The compounds of formula I also have use as broad spectrum crop antifingal agents and are effective on a broad spectrum of phytopathogenic fungi, in particular those from the class consisting of: *Deuteromycetes* (e.g. *Botrytis* spp., *Septoria* spp., *Pyricularia* spp., *Stagnospora* spp., *Helminthosporium* spp., *Fusarium* spp., *Cercospora* spp., *Rhynchosporium*, spp. *Pseudocercosporella*, spp. and *Alternaria* spp.); *Basidiomycetes* (e.g. *Puccinia* spp., *Rhizoctonia* spp., and *Hemileia*); *Ascomycetes* (e.g. *Venturia* spp., *Podospharera* spp., *Erysiphe* spp., *Monilinia* spp. and *Uncinula* spp.); and *Oomycetes* (e.g. *Phytophthora* spp., *Pemospora* spp., *Bremia* spp., *Pythium* spp., and *Plasmopara* spp.). The foregoing list exemplifies the phytopathogenic fungi against which the named compounds demonstrate activity, and is not limiting in any manner. These compounds have very advantageous curative and preventive fungicidal properties for protecting plants, and can be used to inhibit or to destroy the microorganisms occurring on plants or on parts of plants (the fruit, blossom, leaves, stalks, tubers or roots) of different crops of useful plants, while at the same time parts of plants that grow later are also protected against such microorganisms. They can also be used as dressings in the treatment of plant propagation material, especially seed (fruit, tubers, grain) and plant cuttings (for example rice), to provide protection against fungal infections and against phytopathogenic fungi occurring in the soil. Compounds of formula I of the invention are distinguished by the fact that they are especially well tolerated by plants and are environmentally friendly.

Agricultural evaluation of a compound of formula I can be carried out using the following tests.

1. Action Against *Erysiphe graminis* on Wheat.

a) After one-week cultivation, wheat plants are sprayed to run off with a spray mixture (200 ppm active ingredient/20% acetone/0.25% Triton X155). After 2 hours, the treated plants are infected with ascospores shaken from inoculum plants. Fungal attack is evaluated after incubation for 8 days at 22° C. at 50% relative humidity to determine the protection given by the compound.

b) After one-week cultivation, wheat plants are infected with ascospores shaken from inoculum plants. After 24 hours, the wheat plants are sprayed with a spray mixture (200 ppm active ingredient/20% acetone/0.25% Triton X155). Fungal attack is evaluated after incubation for 8 days at 22° C. at 50% relative humidity to determine the degree of curative activity provided by the compound.

c) After one-week cultivation, wheat plants are infected with ascospores shaken from inoculum plants. After 24 hours, the soil in which the wheat plants are growing is drenched with the drench mixture (200 ppm active ingredient/20% acetone/0.25% Triton X155). Fungal attack is evaluated after incubation for 8 days at 22° C. at 50% relative humidity to determine the degree of curative activity provided by the compound.

2. Action Against *Puccinia recondita* on Wheat a) After one-week cultivation, wheat plants sprayed to run off with a spray mixture (200 ppm active ingredient/20% acetone/0.25% Triton X155). After 2 hours, the treated plants are infected with a spore. Fungal attack is evaluated after incubation for one day at 95–100% relative humidity at 20° C. followed by 7 days at 25° C. at 50% relative humidity to determine the protection given by the compound.

b) After one-week cultivation, wheat plants are infected with a spore suspension. After 24 hours, the infected plants are sprayed to run off with a spray mixture (200 ppm active ingredient/20% acetone/0.25% Triton X155. Fungal attack is evaluated after incubation for 1 day at 95–100% relative humidity at 20° C. followed by 7 days at 25° C. at 50% relative humidity to determine the degree of curative activity provided by the compound.

c). After one-week cultivation, wheat plants are infected with a spore suspension. After 24 hours, the soil in which the wheat plants are growing was drenched with the drench mixture (200 ppm active ingredient/20% acetone/0.25% Triton X155). Fungal attack is evaluated after incubation for 1 day at 95–100% relative humidity at 20° C. followed by 7 days at 25° C. at 50% relative humidity to determine the degree of curative activity provided by the compound.

Based on the spectrum of activity, the compounds of the present invention can be used to protect or cure plants of phytopathogenic fungi affecting various useful crops. The following species of plants are suitable for the use described in the scope of the invention of the stated compounds: cereal (e.g. wheat, rye, oat, barley, rice, sorghum and related crops); beet (sugar beet and fodder beet); pomes, dropes and soft fruit (e.g. apples, pears, plums, peaches, almonds, cherries, strawberries, raspberries, and blackberries); leguminous plants (e.g. beans, peas, lentils and soybeans); oil plants (rape, mustard, poppy, olives, sunflowers, coconut, castor oil plants, cocoa beans and groundnuts); curbitats (e.g. cucumber, squash, and melon); fiber plants (e.g. cotton, flax, hemp, and jute); citrus fruit (e.g. oranges, lemons, madarins and grapefruit); vegetables (e.g. lettuce, cabbage, spinach, carrot, asparagus, paprika, onions, tomatoes, and potatoes); lauraceae: (avocados, cinnamon and camphor); or plants such as maize, tobacco, nuts, coffee, sugar cane, tea, vines, hops, bananas and natural rubber plants, as well as ornamentals (flowers, shrubs, broad-leaved trees and evergreens, such as conifers). However, the aforementioned plant species do not constitute a limiting list of plants with respect to spectrum by the stated compounds.

The compounds of formula I are particularly useful for controlling the following plant diseases:

*Erysiphe graminis* in cereals, *Erysiphe cichoracearum* and *Sphaerotheca fuliginea* in cucurbits, *Podosphaera leucotricha* in apples, *Uncinula necator* in vines, *Puccinia* species in cereals, *Rhizoctonia solani* in cotton, Ustilago species in cereals and sugar cane, *Venturia inaequalis* (scab) in apples, Helminthosporium species in cereals, *Septoria nodorum* in wheat, *Botrytis cinerea* (gray mold) in strawberries and grapes, *Cercospora arachidicola* in groundnuts, *Pseudocercosporella herpotrichoides* in wheat and barley, *Pyricularia oryzae* in rice, *Phytophthora infestans* in potatoes and tomatoes, *Fusarium* and *Verticillium* species in various plants, *Plasmopara viticola* in grapes, Alternaria species in fruit and vegetables. The compounds of formula I may also be used for protecting materials (e.g. preservation of timber against *Paecilomyces variotii*).

Pharmaceutical Compositions.

While it is possible that, for use in therapy, compounds of the present invention may be administered as the raw chemical, it is preferable to present the active ingredient in a pharmaceutical composition. The present invention thus further provides a pharmaceutical composition comprising a compound of formula (I) or a pharmaceutically acceptable salt thereof, together with one or more pharmaceutically acceptable carriers thereof and, optionally, other therapeutic and/or prophylactic ingredients. The carrier(s) must be acceptable in the sense of being compatible with the other ingredients of the formulation and not deleterious to the recipient thereof.

The compositions of the present invention include those in a form especially formulated for oral, buccal, parenteral, implant, rectal, topical, ophthalmic or genito-urinary administration or in a form suitable for administration by inhalation or insufflation.

Tablets and capsules for oral administration may contain conventional excipients such as binding agents, for example, syrup, acacia, gelatin, sorbitol, tragacanth, mucilage of starch or polyvinylpyrrolidone; fillers, for example, lactose, sugar, microcrystalline cellulose, maize-starch, calcium phosphate or sorbitol; lubricants, for example, magnesium stearate, stearic acid, talc, polyethylene glycol or silica; disintegrants, for example, potato starch or sodium starch glycollate or crosscarmellose sodium; or wetting agents such as sodium lauryl sulphate. The tablets which include chewable, dispersible or effervescent tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example, almond oil, fractionated coconut oil, oily esters, propylene glycol or ethyl alcohol; and preservatives, for example, methyl or propyl p-hydroxybenzoates or sorbic acid.

For buccal administration the composition may take the form of tablets or lozenges formulated in conventional manner.

The composition according to the present invention may be formulated for parenteral administration by injection or continuous infusion. Formulations for injection may be presented in unit dose form in ampoules, or in multi-dose containers with an added preservative. The compositions may take such forms as suspensions, solutions, or emulsions in oily or aqueous vehicles, and may contain formulatory agents such as suspending, stabilizing and/or dispersing agents. Alternatively the active ingredient may be in powder form for constitution with a suitable vehicle, e.g. sterile, pyrogen-free water, before use.

For administration by inhalation the compositions according to the present invention are conveniently delivered in the form of an aerosol spray presentation from pressurized packs with the use of a suitable propellant, e.g. dichlorodifluoromethane, trichlorofluoromethane, dichlorotetrafluoroethane, carbon dioxide or other suitable gas, or from a nebulizer. In the case of a pressurized aerosol the dosage unit may be determined by providing a valve to deliver a metered amount.

Alternatively, for administration by inhalation the compositions according to the invention may take the form of a dry powder composition, for example a powder mix of the compound and a suitable powder base such as lactose or starch or as a modified physical form of the drug substance alone. The powder composition may be presented in unit dosage form in, for example, capsules or cartridges of e.g. gelatin, or blister packs from which the powder may be administered with the aid of an inhaler or insufflator.

The compositions may take the form of a suppository, e.g. containing a conventional suppository base, or a pessary, e.g. containing a conventional pessary base.

The compositions may also be formulated for topical administration in the form of ointments, creams, gels, lotions, shampoos, powders (including spray powders), pessaries, tampons, sprays, dips, aerosols, drops (e.g. eye, ear or nose drops) or pour-ons. Ointments and creams may, for example, be formulated with an aqueous or oily base with the addition of suitable thickening and/or gelling agents. Ointments for administration to the eye may be manufactured in a sterile manner using sterilized components. Pour-ons may, for example, be formulated for veterinary use in oils containing organic solvents, optionally with formulatory agents, e.g. stabilizing and solubilizing agents. Pessaries and tampons for vaginal insertion may be formulated using conventional techniques and, where appropriate, may contain an effervescent vehicle. Such compositions may also contain other active ingredients such as corticosteroids, antibiotics or antiparasitics as appropriate.

Liquid preparations for intranasal delivery may take the form of solutions or suspensions and may contain conventional excipients such as tonicity adjusting agents, for example, sodium chloride, dextrose or mannitol; preservatives, for example benzalkonium chloride, thiomersal, phenylethyl alcohol; and other formulating agents such as suspending, buffering, stabilizing, dispersing and or flavoring agents.

Transdermal administration may be affected by the design of a suitable system which promotes absorption of the active compound through the skin and would typically consist of a base formulation enclosed within an adhesive stick-on patch comprising backing films, membranes and release liners. Such systems may include absorption enhancers such as alcohols or work by promoting ionotophoresis.

The composition according to the present invention may also be formulated as a depot preparation. Such long acting formulations may be administered by implantation (for example subcutaneously or intramuscularly) or by intramuscular injection. Thus, for example, a compound of the invention may be formulated with suitable polymeric or hydrophobic materials (for example as an emulsion in an acceptable oil) or ion exchange resins, or as sparingly soluble derivatives, for example, as a sparingly soluble salt.

When the compositions comprise dosage units, each unit will preferably contain 0.001 mg to 1000 mg, advantageously 0.01 mg to 400 mg, of active ingredient where a compound of the invention is to be administered orally. The daily dosage as employed for adult human treatment will preferably range from 0.001 mg to 5000 mg of active ingredient, most preferably from 0.01 mg to 2000 mg which may be administered in 1 to 4 daily doses, for example, depending on the route of administration and on the condition of the patient and the disease to be treated.

The compound may be administered by intravenous infusion using, for example, up to 50 mg/kg/day of the active ingredient. The duration of treatment will be dictated by the rate of response rather than by arbitrary number of days.

The compounds of the present invention may also be used in combination with other therapeutic agents, and the invention thus provides, in a further aspect, a combination comprising a compound of the invention together with another therapeutically active agent.

Thus, for example the compounds of the present invention may be used in combination with one or more other antifungal agents, such as polyenes (e.g., amphotericin B, nystatin, and liposomal and lipid forms thereof); azole (e.g., fluconazole, intraconazole, detoconazole, miconazole, clotrimazole, voriconazole, ZD-08070, UK-109496, SCH 56592); purin or pyrimidine nucleotide inhibitors (e.g, 5-fluorocytosine, flucytosine); polyoxin (e.g, nikkomycin Z); a pneumocandin or echinocandin derivative (e.g., cilofungin, anidulafingin (V-echinocandin), 1-[(4R,5S)-5-[(2-aminoethyl)oxy]-$N^2$-(10,12-dimethyl-1-oxotetradecyl)-4-hydroxy-L-ornithine]-5-[(3R)-3-hydroxy-L-ornithine] pneumocandin $B_0$ and caspofingin (CANCIDAS™)); the elongation factor inhibitor (sordarin derivatives); or other cell wall active compound such as one or more immunomodulating agents (e.g., an interferon e.g. (IFN-), interleukine e.g. (IL-1, IL-2, IL-3 and IL-8) and colony stimulating factors, [(G)-CSF, (M)-CSF and (GM)-CSF] and defensines).

Particularly preferred compounds for use with the compounds of the present invention include intraconazole, flucytosine, fluconazole or amphotericin B.

When the compounds of the present invention are administered in combination with another antifungal agent the compounds of the invention and the other fungal agent can be administered at the recommended maximum clinical dosage or at lower doses.

The combinations referred to above may conveniently be presented for use in the form of a pharmaceutical formulation and thus pharmaceutical formulations comprising a combination as defined above together with a pharmaceutically acceptable carrier thereof comprise a further aspect of the invention. The individual components of such combinations may be administered either sequentially or simultaneously in separate or combined pharmaceutical formulations When a compound of the invention is used in combination with a second therapeutic agent against the same condition the dose of each compound may differ from that when the compound is used alone. Appropriate doses will be readily appreciated by those skilled in the art.

Agrochemical Compositions

The compounds of formula I can be used in either an unmodified form or preferably together with adjuvants conventionally employed in the art of agrochemical formulation and are for this purpose forms known mainly as: emulsifiable concentrates, coatable pastes, directly sprayable or dilutable solutions, dilute solution, suspensions (including high-percentage aqueous, oily or other suspensions), dispersions, oil dispersions, broadcasting agents, wettable powders, soluble powders, dusts, granules, and encapsulations. The formulations are prepared in known manner, e.g. by homogeneously mixing and/or grinding the active ingredients with extenders, e.g. solvents, solid carriers and, where appropriate, surface-active compounds (surfactants). Powders, dusts and broadcasting agents may be prepared by mixing or grinding the active ingredients with a solid carrier. Granules, e.g., coated, impregnated or homogeneous granules, may be prepared by bonding the active ingredients to solid carriers.

Suitable solvents are: aromatic hydrocarbons, preferably the fractions containing 8 to 12 carbon atoms, such as xylene mixtures or substituted naphthalenes, chlorinated aromatics such as chlorobenzenes, phthalates, such as dibutyl or dioctyl phthalate, aliphatic hydrocarbons, such as cyclohexane or paraffins, alcohols and glycols and their ethers and esters, such as ethanol, ethylene glycol, ethylene glycol monomethyl or monoethyl ether, ketones such as cyclohexanone, amines such as ethanolamine, strongly polar solvents, such as N-methyl-2-pyrrolidone, dimethyl sulfoxide or dimethylformamide, and vegetable oils or epoxidized vegetable oils, such as epoxidized coconut oil or soybean oil; and water.

Examples of surfactants are: alkali metal, alkaline earth metal and ammonium salts of aromatic sulfonic acids, e.g., ligninsulfonic acid, phenolsulfonic acid, naphthalene-sulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Examples of solid carriers are mineral earths such as silicic acids, silica gels, silicates, talc, kaolin, attapulgus clay, limestone, lime, chalk, bole, loess, clay, dolomite, diatomaceous earth, aluminas calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

The compounds of formula I may be mixed and applied together with other active ingredients, for example herbicides, insecticides, bactericides, nematocides, molluscicides, growth regulators, micronutrients, and fertilizers. The other ingredients may also be one or more fungicides belonging to but not restricted to the following classes of fungicides: carboxamides, benzimidazoles, triazoles, hydroxypyridines, dicarboxamides, phenylamides, thiadiazoles. carbamates, cyano-oximes, cinnamic acid derivatives, morpholines, imidazoles, B-methoxy acrylates and pyridines/pyrimidines. Furthermore, these additional active ingredients may be used as mixtures of several of the preparations, if desired together with other application promoting adjuvants usually used in the art of formulation. Suitable carriers and adjuvants can be solid or liquid and correspond to the substances typically used in formulation technology (e.g. natural or regenerated mineral substances, solvents, disperants, and wetting agents).

The following list of fungicides with which the compounds of formula I may be combined is intended to illustrate possible combinations but not to impose any restrictions. Examples of fungicides which may be combined with the compounds of formula I are: sulfur, dithiocarbamates and their derivatives, such as ferric dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfides, ammonia complex of zinc N,N'-ethylenebisdithiocarbamate, ammonia complex of zinc N,N'-propylenebisdithiocarbamate, zinc N,N'-propylenebisdithiocarbamate and N,N'-polypropylenebis (thiocarbamyl) disulfide; nitro derivative, such as dinitro(1-methylheptyl)-phenyl crotonate, 2-sec-butyl-4,6-dinitrophenyl 3,3-dimethylacrylate, 2-sec-butyl-4,6-dinitrophenyl isopropylcarbonate and diisopropyl 5-nitroisophthalate; heterocyclic substances, such as 2-heptadecylimidazol-2-yl acetate, 2,4-dichloro-6-(o-chloroanilino)-s-triazine, O,O-diethyl phthalimidophosphonothioate, 5-amino-1-[bis-(dimethylamino)-phosphinyl]-3-phenyl-1,2,4-triazole, 2,3-dicyano-1,4-dithioanthraquinone, 2-thio-1,3-dithio[4,5-b]quinoxaline, methyl 1-(butylcarbamyl)-2-benzimidazolecarbamate, 2-methoxycarbonylaminobenzimidazole, 2-(fur-2-yl)-benzimidazole, 2-(thiazol-4-yl)benzimidazole, N-(1,1,2,2-tetrachloroethylthio)-tetrahydrophthalimide, N-trichloromethylthiotetrahydrophthalimide, N-trichloromethylthiophthalimide, N-dichlorofluoromethylthio-N',N'-dimethyl-N-phenylsulfuric acid diamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, 2-thiopyridine 1-oxide, 8-hydroxyquinoline and its copper salt, 2,3-dihydro-5-carboxanilido-6-methyl-1,4-oxathiyne, 2,3-dihydro-5-carboxanilido-6-methyl-1,4-oxathiyne 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, 2,5-dimethyl-N-cyclohexylfuran-3-carboxamide, N-cyclohexyl-N-methoxy-2,5-diethylfuran-3-carboxamide, 2-methylbenzanilide, 2-iodobenzanilide, N-formyl-N-morpholine-2,2,2-trichloroethylacetal, piperazine-1,4-diylbis-(1-(2,2,2-trichloroethyl)-formamide), 1-(3,4-dichloroanilino)-1-formylamino-2,2,2-trichloroethane, 2,6-dimethyl-N-tridecylmorpholine and its salts, 2,6-dimethyl-N-cyclododecylmorpholine and its salts, N[3-(para-tert.-butylphenyl)-2-methylpropyl]-cis-2,6-dimethylmorpholine, N-[3-(para-tert.-butylphenyl)-2-methylpropyl]-piperidine, 1-2-(2,4-dichlorophenyl)-4-ethyl-1,3-dioxolan-2-yl-ethyl]-1H-1,2,4-triazole, 1-[2-(2,4-dichlorophenyl)-4-n-propyl-1,3-dioxolan-2-yl-ethyl]-1H-1,2,4-triazole, N-(n-propyl)-N-(2,4,6-trichlorophenoxyethyl)-N]-imidazolylurea, 1-(4-chlorophenoxy)-3,3-dimethyl-1-(1H-1,2,4-triazol-1-yl)-butan-2-one, 1-(4-chlorophenoxy)-3,3-dimethyl-1-(1H-1,2,4-triazol-1-yl)-butan-2-ol, alpha-(2-chlorophenyl)-alpha-(4-chlorophenyl)-5-pyrimidinemethanol, 5-butyl-(2-dimethylamino-4-hydroxy-6-methylpyrimidine, bis-(p-chlorophenyl)-3-pyridinemethanol, 1,2-bis-(3-ethoxycarbonyl-2-thioureido)-benzene, 1,2-bis-(3-methoxycarbonyl-2-thioureido)-benzene, and various fungicides, such as dodecylguanidine acetate, 3-[3-(3,5-dimethyl-2-oxycyclohexyl)-2-hydroxyethyl]-glutaramide, hexachlorobenzene, DL-methyl-N-(2,6-dimethylphehyl)-N-fur-2-yl alanate, methyl DL-N-(2,6-dimethylphenyl)-N-(2]-methoxyacetyl)-alanate, N-(2,6-dimethylphenyl)-N-chloroacetyl-DL-2-aminobutyrolactone, methyl DL-N-(2,6-dimethylphenyl)-N-(phenylacetyl)-alanate, 5-methyl-5-vinyl-3-(3,5-dichlorophenyl)-2,4-dioxo-1,3-oxazolidine, 3-[3,5-dichlorophenyl]-5-methyl-5-methoxymethyl-1,3-oxazolidine-2,4-dione, 3-(3,5-dichlorophenyl)-1-isopropylcarbamylhydantoin, N-(3,5-dichlorophenyl)-1,2-dimethylcyclopropane-1,2-dicarboximide, 2-cyano-[N-(ethylaminocarbonyl)-2-methoximino]-acetamide, 1-[2-(2,4 dichlorophenyl)-pentyl]-1H-1,2,4-triazole, 2,4-difluoro-a-(1H-1,2,4-triazol-1-ylmethyl)-benzhydryl alcohol, N-(3-chloro-2,6-dinitro-4 trifluoromethylphenyl)-5-trifluoromethyl-3-chloro-2-aminopyridine, and 1-((bis-(4-fluorophenyl)-methylsilyl)-methyl)-1H-1,2,4-triazole.

As with the nature of compositions, the method of application such as spraying, atomizing, dusting, scattering, coating, dressing, and pouring are chosen in accordance with the intended objectives of the application and the prevailing circumstances. One method of applying the active ingredient or agrochemical composition containing at least one of the stated compounds is application to the plants (i.e. foliar application). However, the active ingredient can also penetrate the plant through the roots via the soil (i.e. soil application). This may be in the form of either a liquid application to the soil (drench) or a granular application.

The active ingredient can also be applied to plant propagation material such as seeds (fruits, tubers or grains) or plant cuttings, in either liquid form (coating) or in solid form (dressing). Seeds, for example, can be dressed before sowing. The compounds of the invention can also be applied to grains either by impregnating the grains with a liquid formulation of by coating them with a solid formulation. The composition can also be applied to the locus of planting when planting the propagation material, for example to the seed furrow during sowing.

Advantageous rates of application are normally from about 10 g to about 50 kg of active ingredient (a.i.) per hectare, preferably about 100 g to about 2 kg a.i./ha, most preferably about 100 g to about 600 g a.i./ha. The active ingredients of the stated compounds are typically used in the form of compositions and can be applied to the plant, or to parts of the plant either simultaneously or in succession with further active ingredients. These further active ingredients can be fertilizers, additional micronutrients, or other plant growth affecting compounds. They can, however, also be selective herbicides, insecticides, bactericides, nematocides, insecticides, and molluscicides, as well as other fungicides.

The following examples are provided to more fully illustrate the preparation of the present invention, and as such not to be considered as limiting the invention in any manner set forth in the claims appended hereto.

EXAMPLE 1

4-methoxybenzyl (1R,3aR,4S,8aS)-4-formyl-6-hydroxy-8a-(hydroxymethyl)-3-isopropyl-7-methyl-4,4a,5,6,7,7a,8,8a-octahydro-1,4-methano-s-indacene-3a(1H)-carboxylate (4)

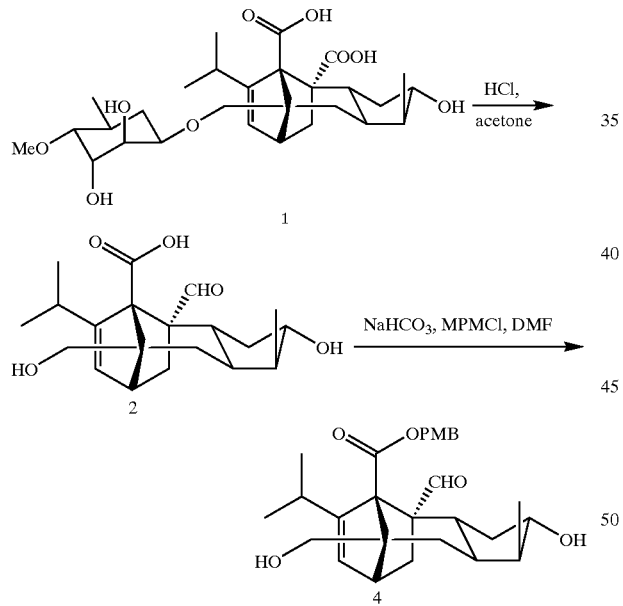

PMB is paramethoxybenzyl.

To a solution of 1 (95.1 mg, 0.19 mmol) in acetone (5 mL) was added 0.5 mL of concentrated HCl. The mixture was stirred at room temperature for one day. After aqueous work-up (EtOAc), the mixture was concentrated in vacuo and was dissolved in DMF (4 mL). About 0.13 mL of p-methoxybenzyl chloride (MPMCl) (0.96 mmol) and NaHCO$_3$ (157.3 mg, 1.87 mmol) were added. The mixture was stirred at room temperature overnight. After aqueous work-up (ether) and purification by a Preparative Thin Layer Chromatography (PTLC), about 58.7 mg of 4 was obtained.

EXAMPLE 2

(1S,3aR,4S,8aS)-6-(acetyloxy)-8a-[(acetyloxy)methyl]-4-formyl-3-isopropyl-7-methyl-4,4a,5,6,7,7a,8,8a-octahydro-1,4-methano-s-indacene-3a(1H)-carboxylic acid (6)

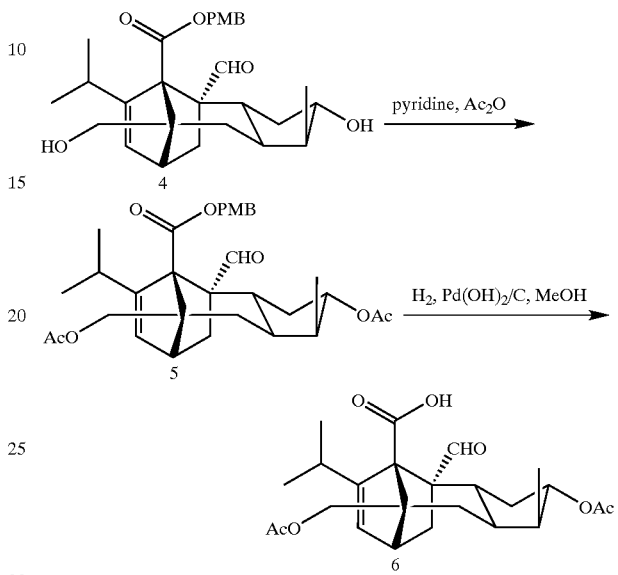

To a solution of 4 (5.0 mg, 0.01 mmol) in pyridine (2 mL) was added 0.5 mL of Ac$_2$O. The mixture was stirred at room temperature overnight. After concentration in vacuo and purification by a PTLC, about 5.2 mg of 5 was obtained. To a solution of 5 (5.2 mg) in CH$_3$OH (1.5 mL) was added Pearlman's catalys (Pd(OH)$_2$/C, 15 mg). The mixture was stirred under H$_2$ (balloon pressure) for about 15 minutes. After filtration and concentration in vacuo, about 3.9 mg of 6 was obtained.

$^1$H NMR (CDCl$_8$): δ0.92 ppm (3H, d, J=6.9), 0.99 (3H, d, J=6.2), 1.06 (3H, d, J=6.2), 1.16 (1H, m), 1.36 (1H, m), 1.80 (1H, m), 1.86 (1H, m), 2.03 (3H, s), 2.05 (3H, s), 2.00–2.10 (4H, m), 2.39 (1H, m), 2.55 (1H, m), 2.79 (1H, m), 4.25 (1H, d, J=10.7), 4.31 (1H, d, J=10.7), 4.75 (1H, m), 6.15 (1H, br s), 9.60 (1H, s).

EXAMPLE 3

(1S,3aR,4S,8aS)-6-(methoxy)-8a-[(methoxy)methyl]-4-formyl-3-isopropyl-7-methyl-4,4a,5,6,7,7a,8,8a-octahydro-1,4-methano-s-indacene-3a(1H)-carboxylic acid (8)

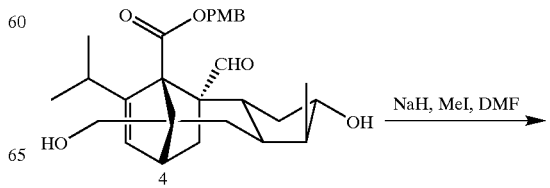

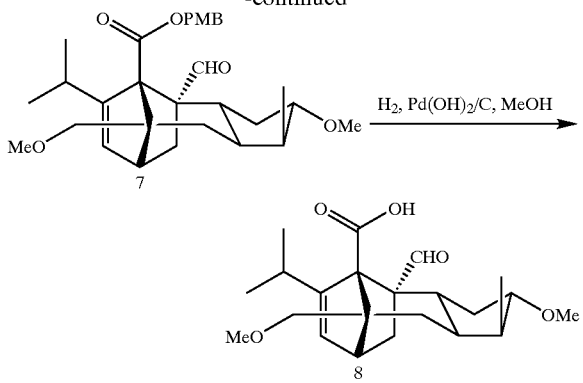

To a solution of 4 (5.0 mg, 0.01 mmol) in DMF (2 mL) was added CH₃I (0.02 mL, 0.3 mmol) and NaH (10 mg of a 60% oil dispersion, 0.25 mmol). The mixture was stirred at room temperature overnight. After aqueous work-up (ether) and purification by a PTLC, about 4.7 mg of 7 was obtained, which was dissolved in 1.5 mL of CH₃OH. Pearlman's catalyst (15 mg) was added and the mixture was stirred under H₂ (balloon pressure) for about 15 minutes. After filtration and concentration in vacuo, about 4.7 mg of 8 was obtained.

$^1$H NMR (CDCl₃): δ0.89 ppm (3H, d, J=7.6), 1.00 (3H, d, J=6.7), 1.04 (3H, d, J=6.6), 1.30 (2H, m), 1.60 (1H, m), 2.00–2.18 (5H, m), 2.30–2.50 (3H, m), 3.29 (3H, s), 3.42 (3H, s), 3.45 (1H, m), 3.56 (1H, d, J=9.1), 3.97 (1H, d, J=9.1), 6.10 (1H, s), 9.79 (1H, s).

EXAMPLE 4

(1S,3aR,4S,8aS)-6-(propoxy)-8a-[(propoxy)methyl]-4-formyl-3-isopropyl-7-methyl-4,4a,5,6,7,7a,8,8a-octahydro-1,4-methano-s-indacene-3a(1H)-carboxylic acid (10)

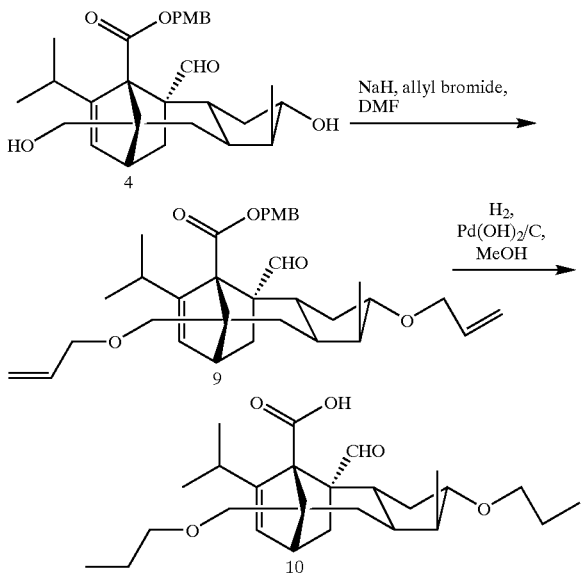

To a solution of 4 (5.5 mg, 0.012 mmol) in DMF (2 mL) was added allyl bromide (0.02 mL, 0.23 mmol) and NaH (5 mg of a 60% oil dispersion, 0.13 mmol). The mixture was stirred at room temperature overnight. After aqueous work-up (ether) and a PTLC, about 5.7 mg of 9 was obtained and was dissolved in CH₃OH (1.5 mL). Pearlman's catalyst (15 mg) was added. The mixture was stirred under H₂ (balloon pressure) for about 15 minutes. After filtration and concentration in vacuo, about 5.5 mg of 10 was obtained.

$^1$H NMR (CDCl₈): δ0.92 ppm (3H, t, J=6.7), 0.94 (3H, d, J=7.0), 0.96 (3H, t, J=6.9), 0.98 (3H, d, J=6.8), 1.02 (3H, d, J=6.7), 1.28 (1H, d, J=12.6), 1.56–1.70 (6H, m), 2.00–2.20 (5H, m), 2.34–2.50 (3H, m), 3.27 (1H, d, J=9.2), 3.30 (2H, m), 3.46 (2H, m), 3.52 (1H, m), 4.00 (1H, d, J=9.2), 6.09 (1H, d, J=3.2), 9.81 (1H, s).

EXAMPLE 5

4-methoxybenzyl (1R,3aR,4S,8aS)-6-{[tert-butyl(dimethyl)silyl]oxy}-4-formyl-8a-(hydroxymethyl)-3-isopropyl-7-methyl-4,4a,5,6,7,7a,8,8a-octahydro-1,4-methano-s-indacene-3a(1H)-carboxylate (11)

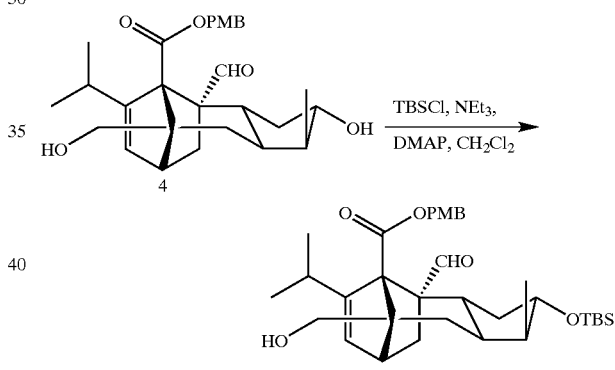

To a solution of 4 (100 mg, 0.21 mmol) in CH₂Cl₂ (10 mL) was added Net₃ (0.045 mL, 0.32 mmol), tert-butyldimethylsilyl chloride (TBSCl) (35.4 mg, 0.23 mmol) and 4-dimethylaminopyridine (DMAP) (2 mg, 0.016 mmol). The mixture was stirred at room temperature overnight. After purification by chromatography about 80.8 mg of 11 was obtained and about 15 mg of 4 was recovered.

$^1$H NMR (CDCl₃): δ0.01 ppm (3H, s), 0.02 (3H, s), 0.52 (3H, d, J=6.7), 0.85 (3H, d, J=6.6), 0.88 (9H, s), 0.96 (1H, m), 1.04 (3H, d, J=6.6), 1.19 (1H, d, J=12.9), 1.44 (1H, m), 1.62 (1H, dd, J=6.4, 14.6), 1.77 (1H, m), 1.82 (1H, dd, J=13, 14), 2.09 (2H, m), 2.30 (2H, m), 2.56 (1H, t, J=3.6), 2.78 (1H, br d, J=7.8), 3.46 (1H, m), 3.62 (1H, t, J=5.8), 3.83 (3H, s), 3.90 (1H, d, J=11.7), 5.05 (1H, d, J=11.7), 5.30 (1H, d, J=11.7), 6.10 (1H, d, J=2.1), 6.89 (2H, d, J=8.5), 7.35 (2H, d, J=8.5), 9.51 (1H, s).

EXAMPLE 6

4-methoxybenzyl (1R,3aR,4S,8aS)-8a-(butoxymethyl)-4-formyl-6-hydoxy-3-isopropyl-7-methyl-4,4a,5,6,7,7a,8,8a-octahydro-1,4-methano-s-indacene-3a(1H)-carboxylate (13)

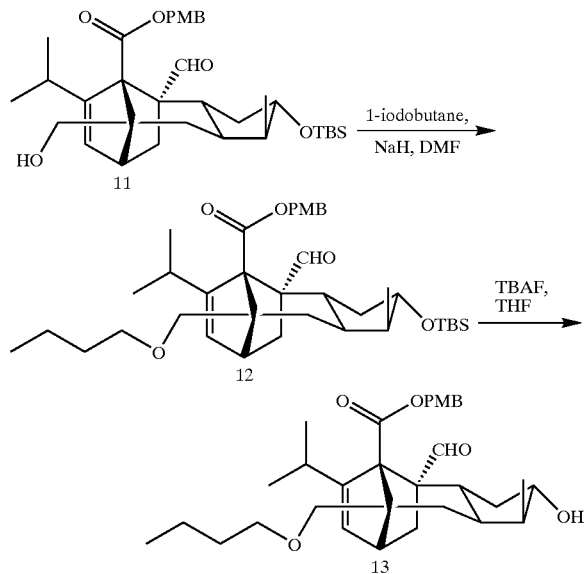

To a solution of 11 (9.9 mg, 0.017 mmol) in DMF (10 mL) was added 1-iodobutane (0.2 mL, 1.75 mmol) and NaH (100 mg of a 60% oil dispersion, 2.5 mmol). The mixture was stirred at room temperature overnight. After aqueous work-up (ether) and a PTLC purification, about 9.9 mg of 12 was obtained and was dissolved in 10 mL of THF. Tetrabutylammonium fluoride (TBAF) (1.5 mL of a 1M solution in THF, 1.5 mmol) was added. The mixture was stirred at room temperature for about two hours. After concentration in vacuo and purification by a PTLC, about 7.2 mg of 13 was obtained.

$^1$H NMR (CDCl$_3$): δ0.55 ppm (3H, d, J=7.6 Hz), 0.85 (3H, d, J=6.6), 0.92 (3H, t, J=7.4), 1.05 (3H, d, J=6.8), 1.23 (1H, d, J=12.6), 1.30–1.40 (3H, m), 1.42–1.50 (3H, m), 1.60 (2H, m), 1.78 (1H, m), 1.92 (1H, dd, J=6.2, 14.2), 2.00 (2H, m), 2.28 (1H, m), 2.45 (1H, m), 2.50 (1H, m), 2.81 (1H, m), 3.30 (1H, m), 3.37 (1H, d, J=8.9), 3.60 (1H, d, J=8.9), 3.78 (1H, t, J=5.8), 3.80 (3H, s), 5.07 (1H, d, J=11.5), 5.18 (1H, d, J=11.5), 6.10 (1H, d, J=2.3), 6.89 (2H, d, J=8.7), 7.33 (2H, d, J=8.7), 9.52 (1H, s).

EXAMPLE 7

(1R,3aR,4S,8aS)-6-(butoxymethyl)-4-formyl-6-hydroxy-3-isopropyl-7-methyl-4,4a,5,6,7,7a,8,8a-octahydro-1,4-methano-s-indacene-3a(1H)-carboxylic acid (14)

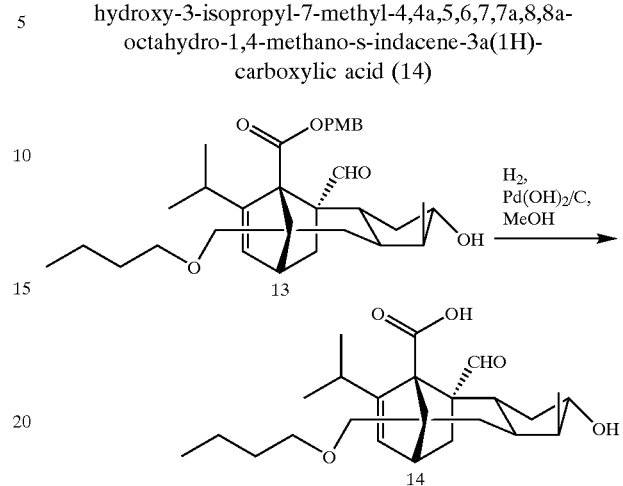

To a solution of 13 (2 mg, 0.0038 mmol) in CH$_3$OH (2 mL) was added Pearlman's catalyst (10 mg). The mixture was stirred under H$_2$ (balloon pressure) for about 15 minutes. After filtration and concentration in vacuo, about 1.5 mg of 14 was obtained.

$^1$H NMR (CDCl$_1$): δ0.89 ppm (3H, d, J=7.6 Hz), 0.90 (3H, t, J=7.4), 1.00 (3H, d, J=6.6), 1.04 (3H, d, J=6.8), 1.30–1.40 (2H, m), 1.50–1.80 (4H, m), 1.95 (1H, m), 2.05 (1H, m), 2.10 (1H, m), 2.18 (1H, m), 2.25 (1H, m), 2.38 (1H, m), 2.42 (1H, m), 2.54 (2H, m), 3.28 (1H, d, J=9.3), 3.52 (2H, m), 4.00 (1H, m), 4.01 (1H, d, J=9.3), 6.10 (1H, d, J=2.0), 9.80 (1H, s).

EXAMPLE 8

(1R,3aR,4S,8aS)-8a-(butoxymethyl)-6-chloro-4-formyl-3-isopropyl-7-methyl-4,4a,5,6,7,7a,8,8a-octahydro-1,4-methano-s-indacene-3a(1H)-carboxylic acid (16)

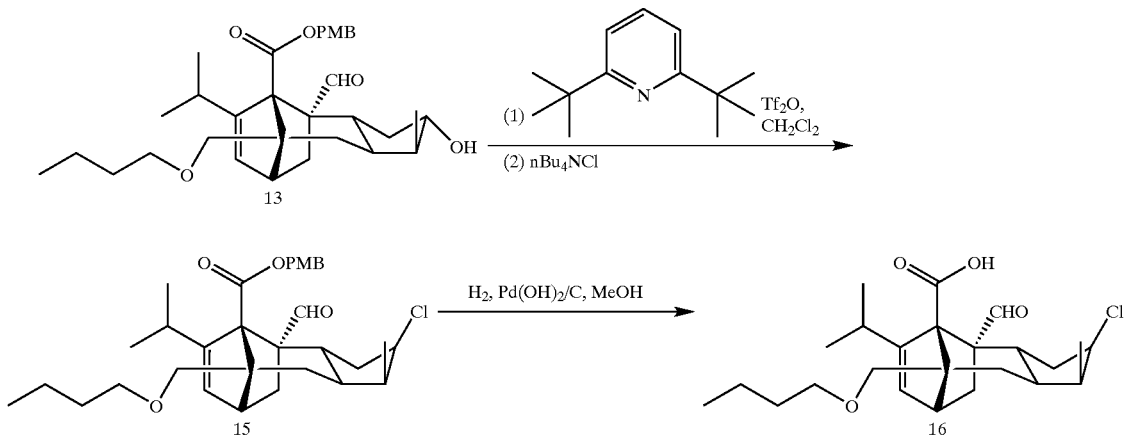

To a solution of 13 (8 mg, 0.015 mmol) in CH$_2$Cl$_2$ (2 mL) was added 2,6-di-tert-butylpyridine (0.007 mL, 0.031 mmol) and Tf$_2$O (0.004 mL, 0.024 mmol) at about 0° C. The mixture was stirred at about 0° C. for about 30 minutes. Tetrabutylammonium chloride (70 mg, 0.31 mmol) was added. The mixture was stirred at room temperature overnight. After aqueous work-up (ether) and purification by a PTLC, about 6.6 mg of 15 was obtained. To a solution of 15 (4.0 mg, 0.0074 mmol) in CH$_3$OH (2 mL) was added Pearlman's catalyst (10 mg). The mixture was stirred under H$_2$ (balloon pressure) for about 15 minutes. After filtration and concentration in vacuo, about 3.0 mg of 16 was obtained.

$^1$H NMR (CDCl): δ0.94 ppm (3H, t, J=7.3 Hz), 1.00 (3H, d, J=6.8), 1.01 (3H, d, J=7.0), 1.07 (3H, d, J=6.6), 1.26 (1H, d, J=12.8), 1.38 (2H, m), 1.58–1.70 (3H, m), 1.90 (2H, m), 1.98 (1H, m), 2.16 (1H, t, J=12.8), 2.25 (1H, m), 2.40 (2H, m), 2.43 (1H, m), 2.50 (1H, m), 3.28 (1H, d, J=9.2), 3.50 (2H, m), 4.00 (1H, d, J=9.2), 4.49 (1H, m), 6.11 (1H, d, J=1.1), 9.75 (1H, s).

mmol) and Tf$_2$O (0.004 mL, 0.024 mmol) at about 0° C. The mixture was stirred at about 0° C. for about 30 minutes. To the mixtures was added tetrabutylammonium azide (1.5 mL of a 0.1M solution in toluene, 0.15 mmol). The mixture was stirred at room temperature for one day. After concentration in vacuo and purification by a PTLC, about 7.1 mg of 17 was obtained. The azido-compound 17 (2.5 mg, 0.0046 mmol) was dissolved in 2 mL of formic acid. The mixture was stirred at room temperature for about 30 minutes. After concentration in vacuo and purification by a PTLC, about 1.7 mg of 18 was obtained.

$^1$H NMR (CDCl$_3$): δ0.91 ppm (3H, d, J=7.3 Hz), 0.93 (3H, t, J=7.1), 1.00 (3H, d, J=6.9), 1.07 (3H, d, J=6.9), 1.25 (2H, m), 1.38 (2H, m), 1.60 (3H, m), 1.92 (1H, m), 1.95 (1H, m), 2.08 (1H, m), 2.15 (1H, m), 2.32–2.45 (4H, m), 3.27 (1H, d, J=9.2), 3.50 (2H, m), 4.01 (1H, d, J=9.2), 4.14 (1H, m), 6.11 (1H, d, J=2.1), 9.76 (1H, s).

EXAMPLE 9

(1R,3aR,4S,8aS)-8a-(butoxymethyl)-6-azido-4-formyl-3-isopropyl-7-methyl-4,4a,5,6,7,7a,8,8a-octahydro-1,4-methano-s-indacene-3a(1H)-carboxylic acid (18)

EXAMPLE 10

(1R,3aR,4S,8aS)-8a-(butoxmethyl)-4-formyl-6-hydroxy-3-isopropyl-7-methyl-4,4a,5,6,7,7a,8,8a-octahydro-1,4-methano-s-indacene-3a(1H)-carboxylic acid (20)

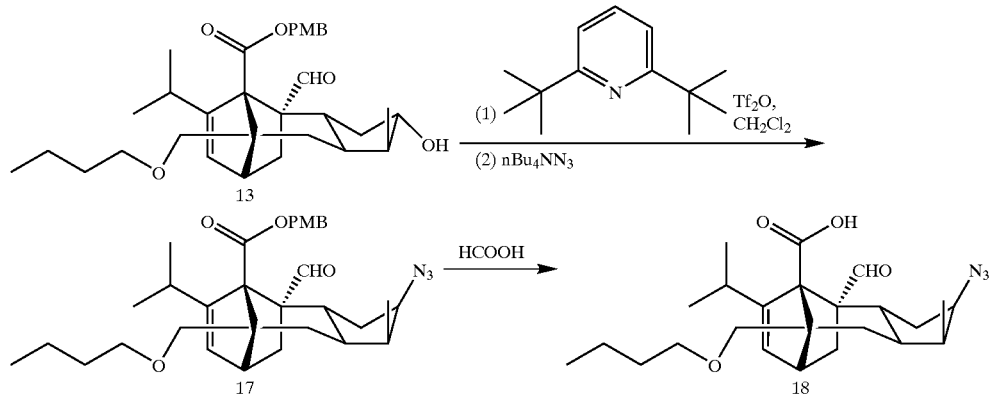

To a solution of 13 (8 mg, 0.015 mmol) in CH$_2$Cl$_2$ (2 mL) was added 2,6-di-tert-butylpyridine (0.007 mL, 0.031

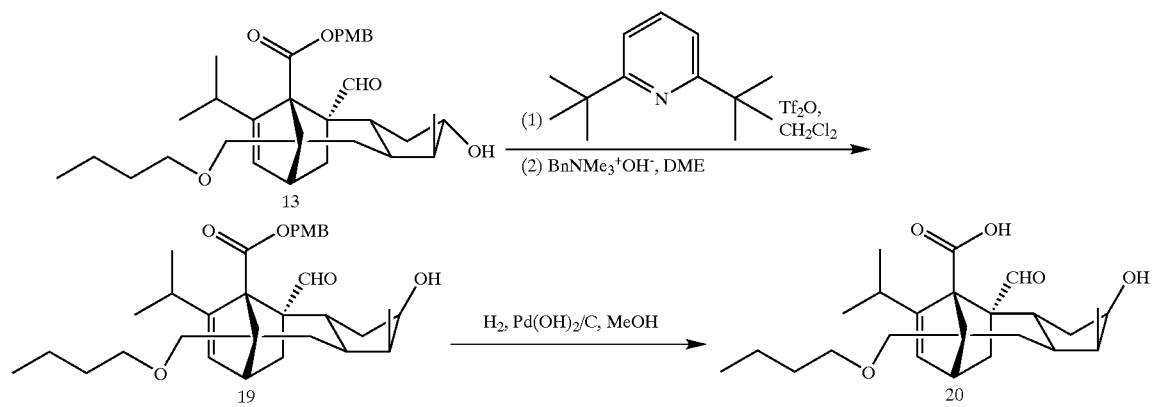

To a solution of 13 (15 mg, 0.029 mmol) in CH₂Cl₂ (3 mL) was added 2,6-di-tert-butylpyridine (0.013 mL, 0.058 mmol) and Tf₂O (0.007 mL, 0.042 mmol) at about 0° C. The mixture was stirred at about 0° C. for about 30 minutes. To the mixture was added ethylene glycol dimethyl ether (DME) (3 mL) and triton B (150 mg of a 40% solution in water, 0.36 mmol). The mixture was stirred at room temperature for about one day. After aqueous work-up (CH₂Cl₂) and purification by a PTLC, about 10 mg of 19 was obtained. To a solution of 19 (2.0 mg, 0.0038 mmol) in CH₃OH (2 mL) was added Pearlman's catalyst (10 mg). The mixture was stirred under H₂ (balloon pressure) for about 15 minutes. After filtration and concentration in vacuo, about 1.5 mg of 20 was obtained.

¹H NMR (CDCl₃): δ0.90 ppm (3H, d, J=7.0 Hz), 0.92 (3H, t, J=6.8), 0.98 (3H, d, J=6.7), 1.02 (3H, d, J=6.7), 1.30–1.40 (2H, m), 1.45–1.80 (4H, m), 1.80–2.00 (3H, m), 2.16 (1H, t, J=13.1), 2.30–2.42 (5H, m), 3.27 (1H, d, J=8.9), 3.48–3.60 (2H, m), 4.01 (1H, d, J=8.9), 4.42 (1H, t, J=1.1), 6.09 (1H), d, J=2.5), 9.81 (1H, s).

EXAMPLE 11

(1R,3aR,4S,8aS)-8a-(butoxymethyl)-4-formyl-3-isopropyl-6-methoxy-7-methyl-4,4a,5,6,7,7a,8,8a-octahydro-1,4-methano-s-indacene-3a(1H)-carboxylic acid (22)

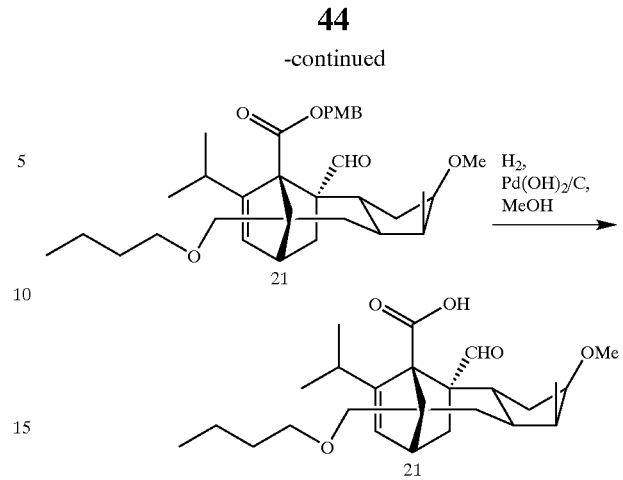

To a solution of 19 (2 mg, 0.0038 mmol) in DMF (2 mL) was added CH₃I (0.01 mL, 0.16 mmol) and NaH (5 mg of a 60% oil dispersion, 0.13 mmol). The mixture was stirred at room temperature overnight. After aqueous work-up (ether) and purification by a PTLC, about 1.9 mg of 21 was obtained. To a solution of 21 (1.9 mg, 0.0035 mmol) in CH₃OH (2 mL) was added Pearlman's catalyst (10 mg). The mixture was stirred under H₂ (balloon pressure) for about 15 minutes. After filtration and concentration in vacuo, about 1.4 mg of 22 was obtained.

¹H NMR (CDCl): δ0.86 ppm (3H, d, J=7.3 Hz), 0.93 (3H, t, J=7.3), 0.99 (3H, d, J=6.9), 1.06 (3H, d, J=6.6), 1.28 (2H, m), 1.38 (2H, m), 1.42 (1H, m), 1.60 (2H, m), 1.90 (3H, m), 2.17 (1H, t, J=13.2), 2.38 (2H, m), 2.41 (2H, m), 3.26 (1H, d, J=9.2), 3.30 (3H, s), 3.45–3.57 (2H, m), 3.86 (1H, m), 4.00 (1H, d, J=9.2), 6.07 (1H, d, J=2.8), 9.84 (1H, s).

EXAMPLE 12

(1R,3aR,4S,8aS)-8a-(butoxymethyl)-6-fluoro-4-formyl-3-isopropyl-7-methyl-4,4a,5,6,7,7a,8,8a-octahydro-1,4-methano-s-indacene-3a(1H)-carboxylic acid (24)

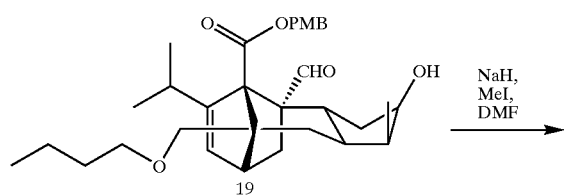

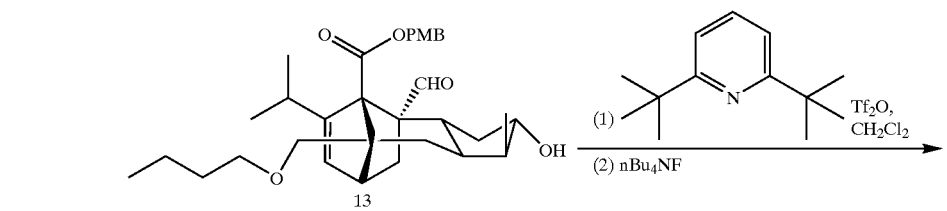

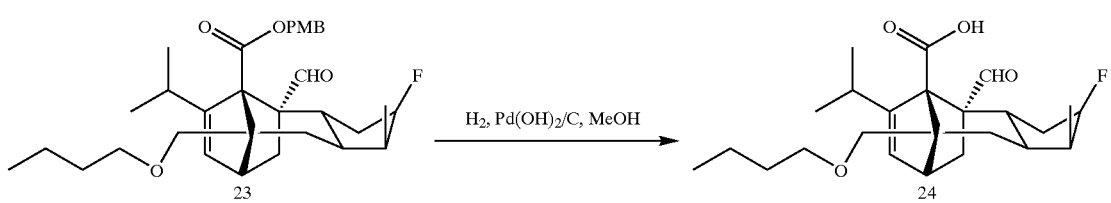

To a solution of 13 (8 mg, 0.015 mmol) in $CH_2Cl_2$ (2 mL) was added 2,6-di-tert-butylpyridine (0.007 mL, 0.031 mmol) and $Tf_2O$ (0.004 mL, 0.024 mmol) at about 0° C. The mixture was stirred at about 0° C. for about 30 minutes. To the mixture was added THF (1 mL) and tetrabutylammonium fluoride (0.3 mL of a 1M THF solution, 0.3 mmol) was added. The mixture was stirred at room temperature overnight. After concentration in vacuo and purification by a PTLC, about 6.5 mg of 23 was obtained. To a solution of 23 (4.0 mg, 0.0076 mmol) in $CH_3OH$ (2 mL) was added Pearlman's catalyst (10 mg). The mixture was stirred under $H_2$ (balloon pressure) for about 15 minutes. After filtration and concentration in vacuo, about 2.9 mg of 24 was obtained.

$^1$H NMR ($CDCl_3$): δ0.92 ppm (3H, d, J=7.0), 0.93 (3H, t, J=7.1), 1.00 (3H, d, J=7.0), 1.07 (3H, d, J=7.0), 1.26 (2H, m), 1.39 (2H, m), 1.60 (2H, m), 1.87 (2H, m), 2.18 (1H, t, J=13.2), 2.21 (1H, m), 2.42 (4H, m), 3.27 (1H, J=9.7), 3.52 (3H, m), 4.01 (1H, d, J=9.2), 5.18 (1H, dt, J=53.7, 7.1), 6.10 (1H, d, J=2.3), 9.82 (1H, s).

EXAMPLE 13

(1R,3aR,4S,8aS)-8a-(butoxymethyl)-6-cyano-4-formyl-3-isopropyl-7-methyl-4,4a,5,6,7,7a,8,8a-octahydro-1,4-methano-s-indacene-3a(1H)-carboxylic acid (26)

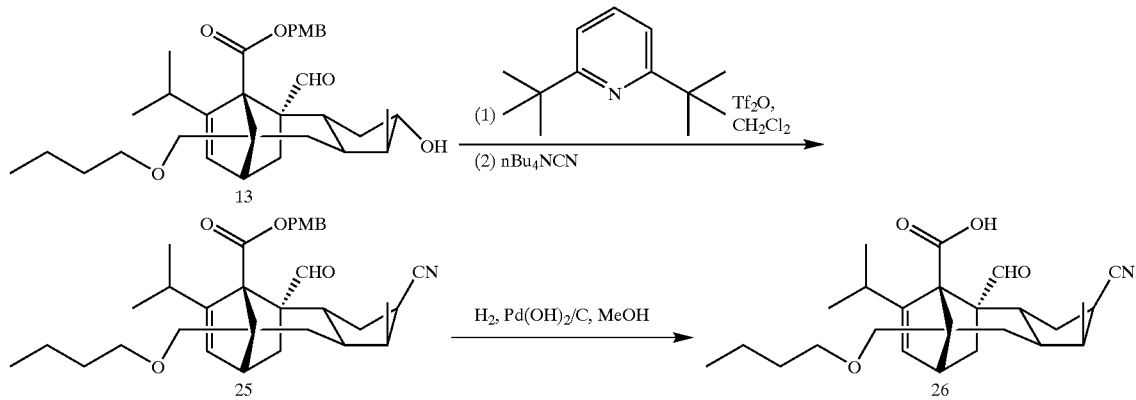

To a solution of 13 (8 mg, 0.015 mmol) in $CH_2Cl_2$ (2 mL) was added 2,6-di-tert-butylpyridine (0.007 mL, 0.031 mmol) and $Tf_2O$ (0.004 mL, 0.024 mmol) at about 0° C. The mixture was stirred at about 0° C. for about 30 minutes. To the mixture were added THF (1 mL) and tetrabutylammonium cyanide (82 mg, 0.31 mmol). The mixture was stirred at room temperature overnight. After concentration in vacuo and purification by a PTLC, about 6.4 mg of 25 was obtained. To a solution of 25 (4.0 mg, 0.0075 mmol) in $CH_3OH$ (2 mL) was added Pearlman's catalyst (10 mg). The mixture was stirred under $H_2$ (balloon pressure) for about 15 minutes. After filtration and concentration in vacuo, about 2.9 mg of 26 was obtained.

$^1$H NMR ($CDCl_3$): δ0.94 ppm (3H, t, J=7.3), 1.01 (3H, d, J=6.6), 1.08 (3H, d, J=7.1), 1.10 (3H, d, J=8.0), 1.26 (2H, m), 1.39 (2H, m), 1.61 (2H, m), 1.68 (2H, m), 1.90 (2H, m), 2.14 (1H, t, J=13.2), 2.30–2.50 (4H, m), 3.16 (1H, m), 3.30 (1H, d, J=9.4), 3.50 (2H, m), 4.00 (1H, d, J=9.4), 6.13 (1H, d, J=2.1), 9.7 (1H, s).

EXAMPLE 14

(1R,3aR,4S,8aS)-8a-(butoxymethyl)-6-animo-4-formyl-3-isopropyl-7-methyl-4,4a,5,6,7,7a8,8a-octahydro-1,4-methano-s-indacene-3a(1H)-carboxylic acid, TFA salt (28)

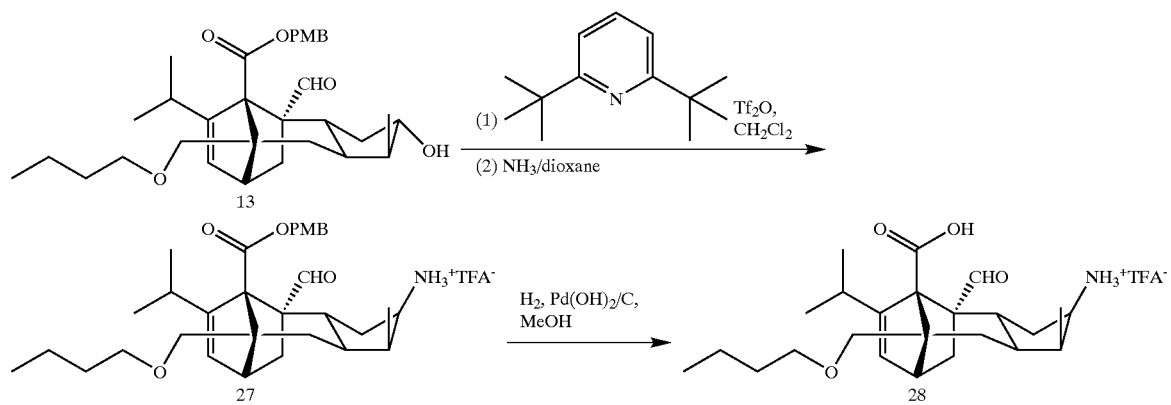

To a solution of 13 (4.9 mg, 0.0094 mmol) in $CH_2Cl_2$ (2 mL) was added 2,6-di-tert-butylpyridine (0.05 mL, 0.22 mmol) and $Tf_2O$ (0.02 mL, 0.12 mmol) at about 0° C. The mixture was stirred at about 0° C. for about 30 minutes. To the mixture was added $NH_3$ (2 mL of a 0.5M solution in dioxane, 1 mmol). The mixture was stirred at room temperature overnight. After concentration in vacuo and purification by a HPLC, about 3.0 mg of 27 (as its triflate salt) was obtained. To a solution of 27 (3.0 mg, 0.0057 mmol) in $CH_3OH$ (2 mL) was added Pearlman's catalyst (10 mg). The mixture was stirred under $H_2$ (balloon pressure) for about 15 minutes. After filtration and concentration in vacuo, about 1.5 mg of 28 was obtained.

$^1H$ NMR ($CDCl_3$): δ0.90 ppm (3H, d, J=7.2), 0.92 (3H, t, J=7.0), 1.01 (3H, d, J=6.8), 1.03 (3H, d, J=6.9), 1.20–1.40 (4H, m), 1.50 (2H, m), 1.60 (2H, m), 1.70–2.00 (4H, m), 2.25 (1H, m), 2.38 (1H, m), 2.50 (1H, m), 2.76 (1H, m), 3.30 (1H, m), 3.50(1H, d, J=8.9), 3.70 (1H, d, J=8.9), 3.71 (1H, m), 6.12 (1H, d, J=2.0), 9.45 (1H, s).

MS: m/z=404 (M+H).

EXAMPLE 15

Preparation of 7-methyl-3-methylenehexahydro-2H-furo[2,3-c]pyran-5-yl(1E)-2,2,2-trichloroethanimidoate (37)

Step 1

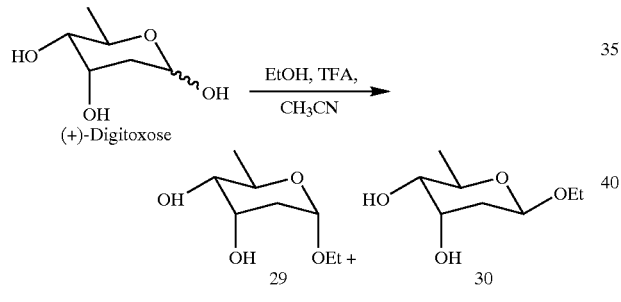

To a solution of (+)-digitoxose (5 g, 0.034 mol) in $CH_3CN$ (200 mL) were added EtOH (50 mL) and trifluoroacetic acid (TFA) (65 mL). The mixture was stirred at room temperature overnight and was then concentrated in vacuo. After chromatography, about 3.2 g of 29 and about 2 g of 30 were obtained. Both isomers could be carried forward, but only 25' 29 was used in this example.

$^1H$ NMR ($CDCl_3$): δ1.25 ppm (3H, t, J=7.1), 1.34 (3H, d, J=6.1), 1.92 (1H, dt, J=14.7, 3.4), 2.18 (1H, m), 3.16 (1H, dd, J=9.9, 3.2), 3.46 (1H, m), 3.60 (1H, br), 3.78 (3H, m), 3.95 (1H, br), 4.91 (1H, d, J=3.5).

Step 2

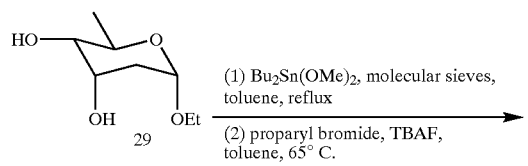

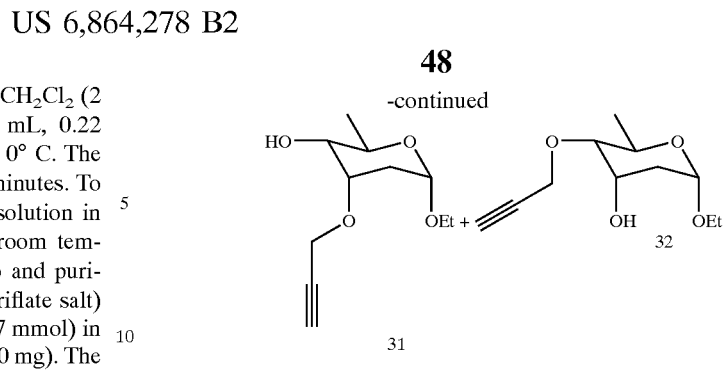

To a solution of 29 (1.79 g, 0.01 mol) in toluene (40 mL) was added 1 g of 4 Å molecular sieves and $Bu_2Sn(OCH_3)_2$ (3.5 mL, 0.015 mol). The mixture was refluxed overnight. At about 6° C., propargyl bromide (3.4 mL of a 80% solution in toluene, 0.031 mol) and tetrabutylammonium fluoride (TBAF) (15 mL of a 1M solution in THF, 0.015 mol) were added. The mixture was stirred at about 65° C. for about one hour. After filtration, concentration in vacuo and chromatography, about 2.03 g of 31 and 32 mixture was obtained, which was used directly in the next step.

Step 3

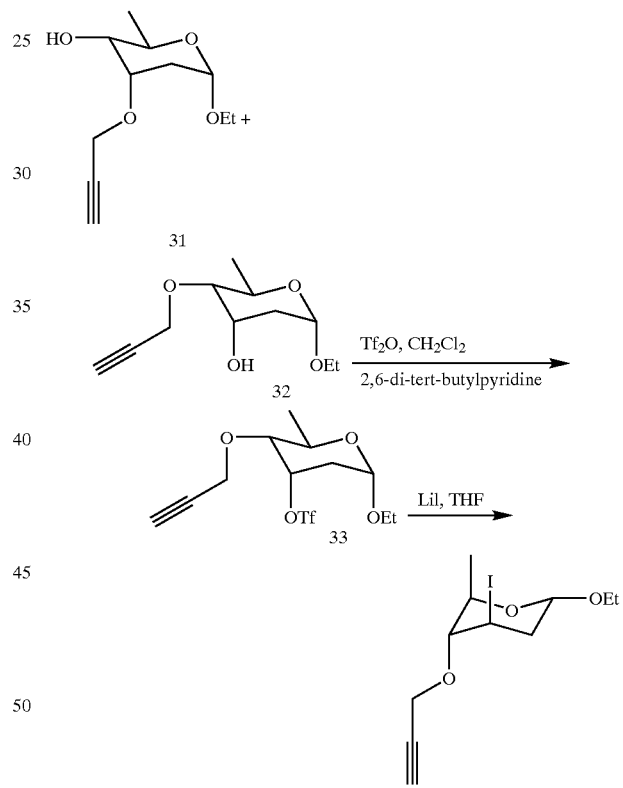

To a solution of the 31 and 32 mixture (2.03 g) was added 2,6-di-tert-butyl-pyridine (4.3 mL, 0.019 mol), followed by $Tf_2O$ (2.1 mL, 0.012 mol) at about 0° C. The mixture was stirred at room temperature for about one hour. After aqueous work-up ($CH_2Cl_2$) and chromatography, about 1.5 g of 33 was obtained. To a solution of 33 (0.96 g, 2.8 mmol) in THF (10 mL) was added LiI (1.9 g, 14 mmol) at room temperature. The mixture was stirred at room temperature for about two hours. After aqueous work-up ($CH_2Cl_2$) and chromatography, about 820 mg of 34 was obtained.

$^1H$ NMR ($CDCl_3$): δ1.20 ppm (3H, t, J=7.1), 1.36 (3H, d, J=6.4), 2.40 (2H, m), 2.55 (2H, m), 3.25 (1H, t, J=10.0), 3.41

(1H, m), 3.63 (1H, m), 3.78 (1H, m), 4.42 (1H, m), 4.48 (1H, dd, J=15.3, 2.5), 4.57 (1H, dd, J=15.3, 2.5).

Step 4

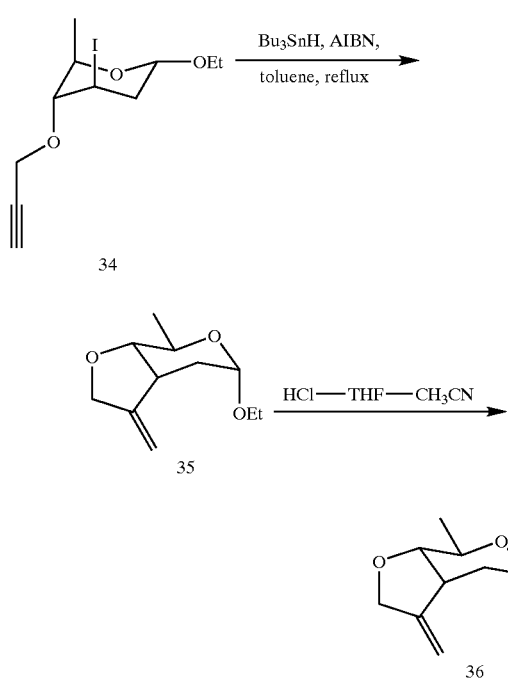

To a solution of 34 (594 mg, 1.82 mmol) in toluene (10 ml) was added Bu₃SnH (0.64 mL, 2.4 mmol) followed by 2,2'-azobisisobutyronitrile (AIBN) (20 mg). The mixture was refluxed for about two hours. After concentration in vacuo and chromatography, about 307 mg of 35 was obtained. To a solution of 35 (100 mg, 0.51 mmol) in THF (5 mL) and CH₃CN (5 mL) was added HCl (5 mL of 1 N solution, 5 mmol). The mixture was stirred at room temperature overnight. After aqueous work-up (CH₂Cl₂) and chromatography, about 76 mg of 36 was obtained in the form of both α- and β-isomers.

Step 5

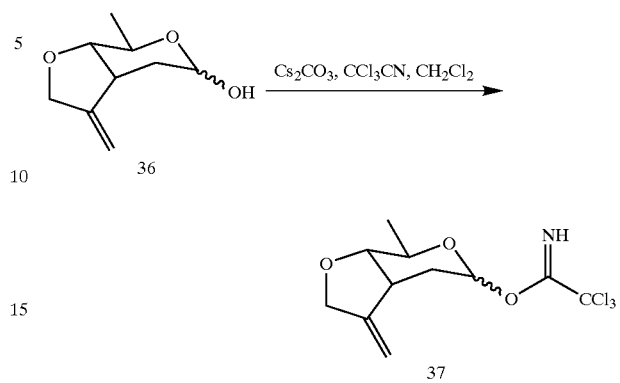

To a solution of 36 (56.5 mg, 0.33 mmol) in CH₂Cl₂ (5 mL) was added Cs₂CO₃ (108 mg, 0.33 mmol) followed by CCl₃CN (0.33 mL, 0.33 mmol). The mixture was stirred at room temperature for about one hour. After filtration, the imidate 37 (7-methyl-3-methylenehexahydro-2H-furo[2,3-c]pyran-5-yl(1E)-2,2,2-trichloroethanimidoate) obtained was concentrated and dried in vacuo and was used directly in the coupling step without further purification.

EXAMPLE 16

(1R,3aR,4S,8aS)-6-chloro-4-formyl-3-isopropyl-7-methyl-8a-{[(7-methyl-3-methylenehexahydro-2H-furo[2,3-c]pyran-5-yl)oxy]methyl}-4,4a,5,6,7,7a8, 8a-octahydro-1,4-methano-s-indacene-3a(1H)-carboxylic acid (44)

Step 1
4-methoxybenzyl (1R,3aR,4S,8aS)-4-formyl-3-isopropyl-6-[(4-methoxybenzyl)oxy]-8a-{[(4-methoxybenzyl)oxy]methyl}-7-methyl-4,4a5,6,7,7a,8,8a-octahydro-1,4-methano-s-indacene-3a(1H)-carboxylate (38)

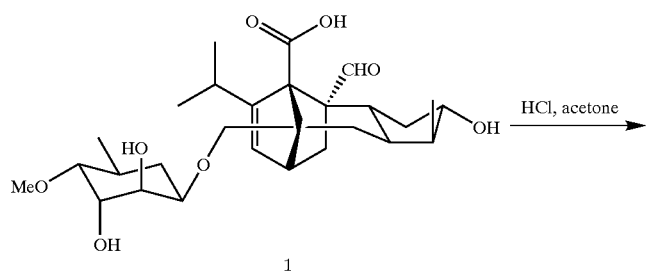

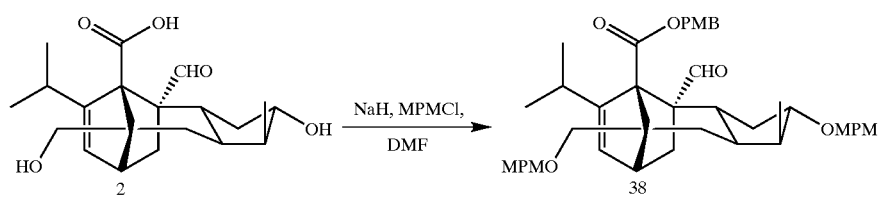

To a solution of 1 (1 g, 1.97 mmol) in acetone (20 mL) was added concentrated HCl (4.5 mL). The mixture was stirred at room temperature for about one day. After aqueous work-up (EtOAc), 946 mg of crude aglycone 2 was obtained and was used directly in the next step without purification. To a solution of the crude aglycone 2 (946 mg) in DMF (20 mL) was added para-methoxybenzyl chloride (MPMCl) (3.7 mL, 27 mmol), followed by NaH (1.1 g of a 60% oil dispersion, 27.5 mmol). The mixture was stirred at room temperature for about one day. After aqueous work-up and chromatography, about 780 mg of 38 was obtained.

$^1$H NMR (CDCl$_3$): δ0.54 ppm (3H, d, J=7.3), 0.86 (3H, d, J=6.6), 1.05 (3H, d, J=6.9), 1.07 (1H, m), 1.18 (1H, d, J=12.8), 1.50 (1H, m), 1.64 (1H, m), 1.84 (1H, t, J=13.6), 2.01 (1H, m), 2.08 (1H, dd, J=12.5, 4.3), 2.30 (1H, m), 2.42 (1H, m), 2.56 (1H, t, J=3.9), 3.43 (1H, t, J=6.1), 3.47 (1H, d, J=11.0), 3.79 (3H, s), 3.82 (3H, s), 3.83 (3H, s), 3.91 (1H, d, J=11.4), 4.37 (4H, s), 4.65 (1H, s), 5.06 (1H, d, J=11.6), 5.27 (1H, d, J=11.4), 6.11 (1H, d, J=2.3), 6.84–7.38 (6H, m), 9.50 (1H, s).

Step 2
4-methoxybenzyl (1R,3aR,4S,8aS)-6-chloro-4-formyl-3-isopropyl-8a-{[(4-methoxybenzyl)oxy]methyl}-7-methyl-4,4a,5,6,7,7a,8,8a-octahydro-1,4-methano-s-indacene-3a(1H)-carboxylate (40)

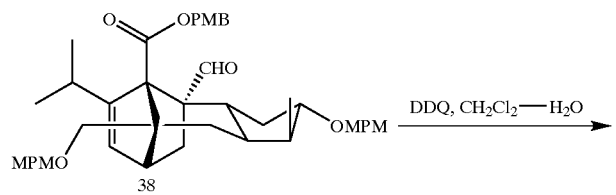

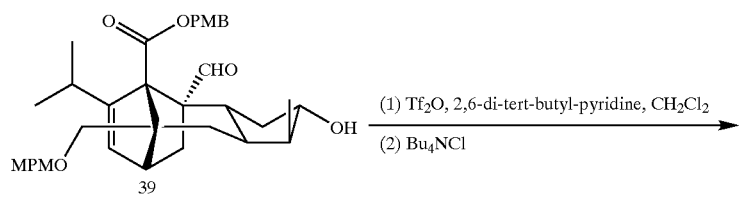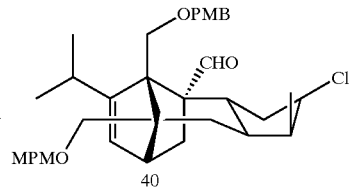

To a solution of 38 (723.1 mg, 1.02 mmol) in CH$_2$Cl$_2$ was added 2,3-dichloro-5,6-dicyano-1,4-benzoquinone (DDQ) (240 mg, 1.06 mmol) and water (1 mL). The mixture was stirred at room temperature for about two hours. After aqueous work-up (CH$_2$Cl$_2$) and chromatography, about 390 mg of 39 was obtained. To a solution of 39 (54.2 mg, 0.092 mol) in CH$_2$Cl$_2$ (5 mL) at about 0° C. was added di-tert-butylpyridine (0.041 mL, 0.18 mmol), followed by Tf$_2$O (0.023 mL, 0.14 mmol). The mixture was stirred at about 0° C. for about 30 minutes. Tetrabutylammonium chloride (512 mg, 1.84 mmol) was then added. The mixture was stirred at room temperature overnight. After aqueous work-up (ether) and PTLC, about 47 mg of 40 was obtained.

$^1$H NMR (CDCl$_3$): δ0.60 ppm (3H, d, J=7.3), 0.76 (3H, d, J=6.7), 1.00 (3H, d, J=6.8), 1.19 (1H, d, J=12.8), 1.68 (1H, t, J=13.3), 1.77 (1H, m), 1.82 (2H, m), 1.97 (2H, m), 2.14 (1H, m), 2.24 (2H, m), 2.84 (1H, t, J=4.0), 3.43 (1H, d, J=9.0), 3.63 (1H, d, J=9.0), 3.82 (3H, s), 3.83 (3H, s), 4.28 (2H, d, J=11.7), 4.39 (2H, d, J=11.7), 4.40 (1H, m), 5.05 (2H, d, J=11.4), 5.20 (2H, d, J=11.4), 6.02 (1H, d, J=2.3), 6.84–7.36 (4H, m), 9.46 (1H, s).

Step 3
(1R,3aR,4S,8aS)-8a-(hydroxyethyl)-4-formyl-3-isopropyl-6-chloro-7-methyl-4,4a,5,6,7,7a,8,8a-octahydro-1,4-methano-s-indacene-3a(1H)-carboxylic acid (41)

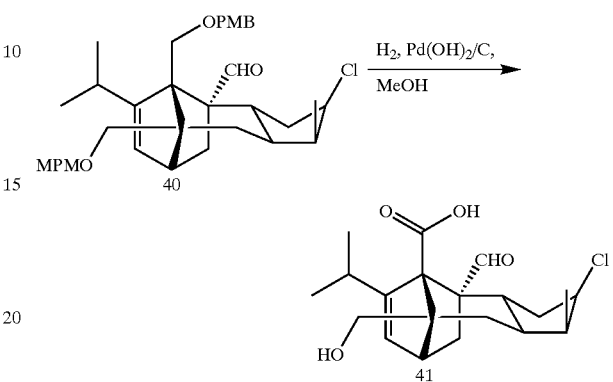

To a solution of 40 (40 mg, 0.066 mmol) in CH$_3$OH (5 mL) was added Pearlman's catalyst (10 mg). The mixture was stirred under hydrogen (balloon pressure) for about 15 minutes. After filtration and concentration in vacuo, about 23.7 mg of 41 was obtained and used directly in the next step.

Step 4
[(2,2-dimethylpropanoyl)oxy]methyl (1R,3aR4S,8aS)-6-chloro-4-formyl-8a-(hydroxymethyl)-3-isopropyl-7-methyl-4,4a,5,6,7,7a,8,8a-octahydro-1,4-methano-s-indacene-3a(1H)-carboxylate (42)

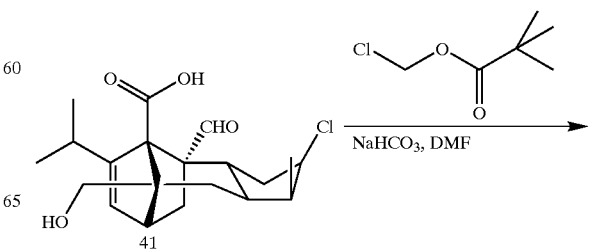

-continued

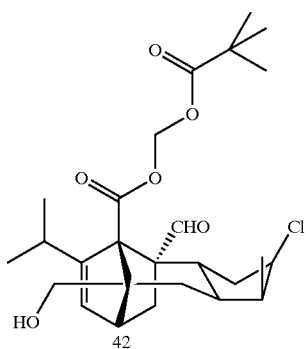

42

To a solution of 41 (23.7 mg) in DMF (5 mL) was added NaHCO3 (109 mg, 1.30 mmol), followed by ClCH$_2$OC(O)CMe$_3$ (0.093 mL, 0.65 mmol). The mixture was stirred at room temperature overnight. After aqueous work-up (ether) and purification by a PTLC, about 26.2 mg of 42 was obtained.

Step 5
(1R,3aR,4S,8aS)-6-chloro-4-formyl-3-isopropyl-7-methyl-8a-{[(7-methylenehexahydro-2H-furo[2,3-c]pyran-5-yl)oxy]methyl}-4,4a,5,6,7,7a,8,8a-octahydro-1,4-methano-s-indacene-3a(1H)-carboxylic acid (44)

To a solution of imidate 37 prepared above in CH$_2$Cl$_2$ (5 mL) was added 42 (16 mg, 0.033 mmol) in CH$_2$Cl$_2$ (1 mL), followed by ZnCl$_2$ (0.6 mL of a 1M solution in ether, 0.6 mmol). The mixture was stirred at room temperature for 2 hours. After aqueous work-up (CH$_2$Cl$_2$) and purification by PTLC, about 12.6 mg of crude product 43 (•- and •-isomers) was obtained. To a solution of this crude product 43 (4 mg) in CH$_3$OH (2 mL) was added K$_2$CO$_2$ (20 mg). The mixture was stirred at room temperature for about two hours. After aqueous work-up (CH$_2$Cl$_2$) and purification by HPLC, about 1 mg of 44 was obtained.

$^1$H NMR (CDCl$_3$): δ1.00 ppm (3H, d, J=7.3), 1.01 (3H, d, J=6.8), 1.06 (3H, d, J=6.9), 1.24 (3H, d, J=6.2), 1.26 (2H, m), 1.78 (1H, dd, J=13.8, 4.8), 1.82–2.08 (4H, m), 2.12 (1H, m), 2.22 (1H, m), 2.40 (3H, m), 2.56 (1H, br s), 3.05 (1H, br s), 3.29 (1H, m), 3.30 (1H, d, J=9.6), 3.79 (1H, t, J=7.8), 4.35 (2H, m), 4.42–4.51 (3H, m), 5.03 (1H, d, J=2.3), 5.10 (1H, d, J=2.3), 6.12 (1H, d, J=2.0), 9.71 (1H, s); and MS: m/z=519 (M+H).

What is claimed is:

1. A compound of formula I:

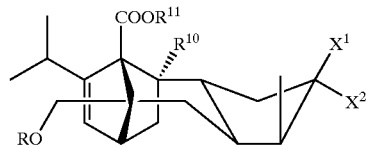

or a pharmaceutically or agriculturally acceptable salt thereof,

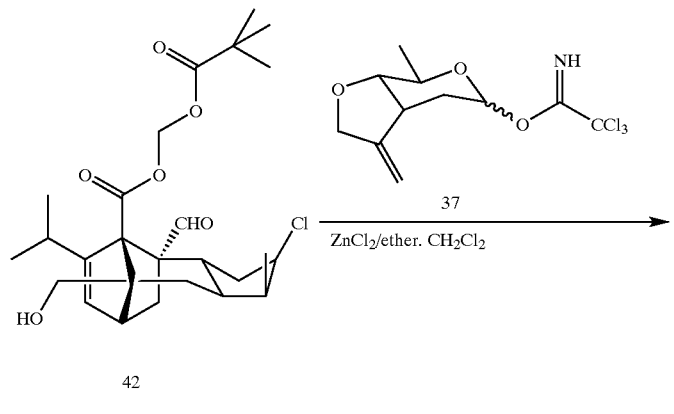

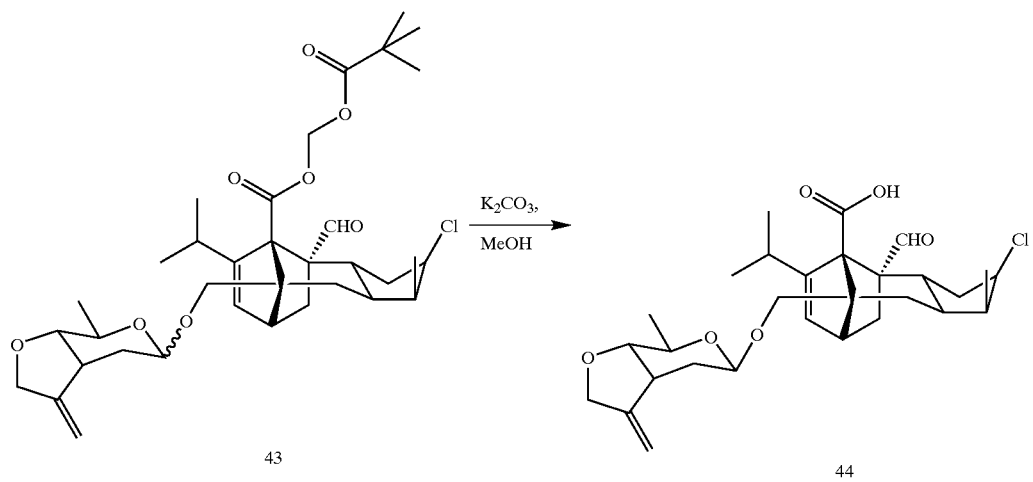

wherein

R is:
- (a) hydrogen,
- (b) C(O)OR$^1$,
- (c) C(O)NR$^2$R$^3$,
- (d) C(O)R$^4$,
- (e) CH(R$^2$)OR$^5$,
- (f) C(R$^6$)(R$^7$)(R$^8$),
- (g)

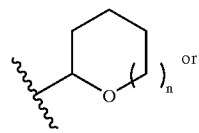

- (h)

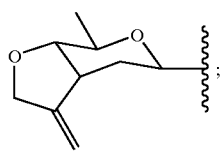

R$^1$ is:
- (a) (C$_1$–C$_{14}$)alkyl,
- (b) (C$_2$–C$_{14}$)alkenyl,
- (c) (C$_2$–C$_{14}$)alkynyl,
- (d) (C$_3$–C$_{20}$)cycloalkyl,
- (e) aryl or
- (f) aryl-(C$_1$–C$_6$)alkyl;

R$^2$ and R$^3$ are independently:
- (a) H or
- (b) R$^1$;

R$^4$ is:
- (a) H,
- (b) R$^1$ or
- (c) (CH$_2$)$_m$NR$^2$R$^3$;

R$^5$ is:
- (a) R$^1$ or
- (b) (CH$_2$)$_x$O(CH$_2$)$_y$H;

R$^6$ is:
- (a) H,
- (b) (C$_1$–C$_{14}$)alkyl,
- (c) aryl,
- (d) aryl-(C$_1$–C$_6$)alkyl,
- (e) (CH$_2$)$_y$CHR$^9$(CH$_2$)$_z$H,
- (f) (CH$_2$)$_y$C≡C(CH$_2$)$_z$H,
- (g) (CH$_2$)$_y$C(R$^7$)=CH(CH$_2$)$_z$H,
- (h) (CH$_2$)$_y$C≡C(CH$_2$)$_m$R$^9$ or
- (i) (CH$_2$)$_y$C(R$^7$)=CH(CH$_2$)$_m$R$^9$;

R$^7$ and R$^8$ are independently:
- (a) H or
- (b) (C$_1$–C$_{14}$)alkyl;

R$^9$ is:
- (a) OH or
- (b) NR$^2$R$^3$;

R$^{10}$ is:
- (a) C(O)H or
- (b) CN;

R$^{11}$ is:
- (a) H,
- (b) —CH$_2$CH=CH$_2$,

- (c)

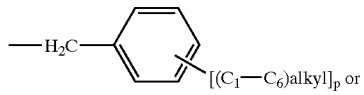

- (d)

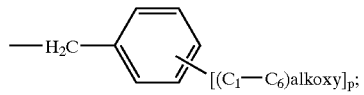

X$^1$ and X$^2$ are independently:
- (a) H, wherein X$^1$ and X$^2$ are not H simultaneously,
- (b) (C$_1$–C$_6$)alkyl,
- (c) (C$_1$–C$_6$)alkoxy,
- (d) (C$_2$–C$_6$)alkenyl optionally substituted with R$^1$,
- (e) OH, wherein X$^1$ and X$^2$ are not OH simultaneously,
- (f) OC[(C$_1$–C$_6$)alkyl]$_3$,
- (g) OC(O)(C$_1$–C$_6$)alkyl,
- (h) halo, wherein halo is F, Cl, Br or I,
- (i) SC(O)(C$_1$–C$_6$)alkyl,
- (j) S(C$_1$–C$_6$)alkyl,
- (k) SH,
- (l) N$_3$,
- (m) N[(C$_1$–C$_6$)alkyl]$_2$,
- (n) N[(C$_1$–C$_6$)alkyl]C(O)(C$_1$–C$_6$)alkyl or
- (o) CN; and wherein X$^1$ and X$^2$ together can be oxo or =CH$_2$;

n is: 0 or 1;
m is: 1–6;
p is: 0–5;
x is: 2–6;
y is: 0–6; and
z is: 0–6.

2. The compound of claim 1, wherein

R is: (a) hydrogen,
- (b) C(O)OR$^1$,
- (c) C(O)NR$^2$R$^3$,
- (d) C(O)R$^4$,
- (e) CH(R$^2$)OR$^5$,
- (f) C(R$^6$)(R$^7$)(R$^8$)
- (g)

- (h)

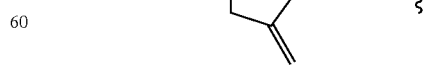

R$^{10}$ is: C(O)H; and
X$^1$ and X$^2$ are independently:
- (a) H, wherein X$^1$ and X$^2$ are not H simultaneously,
- (b) (C$_1$–C$_6$)alkyl, (c) $(C_1-C_6)$alkoxy,
(d) $(C_2-C_6)$alkenyl optionally substituted with $R^1$,
(e) OH, wherein $X^1$ and $X^2$ are not OH simultaneously,
(f) $OC[(C_1-C_6)alkyl]_3$,
(g) $OC(O)(C_1-C_6)$alkyl,
(h) halo, wherein halo is F, Cl, Br or I,
(i) $SC(O)(C_1-C_6)$alkyl,
(j) $S(C_1-C_6)$alkyl,
(k) SH,
(l) $N_3$,
(m) $N[(C_1-C_6)alkyl]_2$,
(n) $N[(C_1-C_6)alkyl]C(O)(C_1-C_6)$alkyl or
(o) CN; and
wherein $X^1$ and $X^2$ together can be oxo or $=CH_2$.

3. The compound of claim 1, wherein
R is: (a) hydrogen,
  (b) $C(O)OR^1$,
  (c) $C(O)NR^2R^3$,
  (d) $C(O)R^4$,
  (e) $CH(R^2)OR^5$,
  (f) $C(R^6)(R^7)(R^8)$,
  (g)

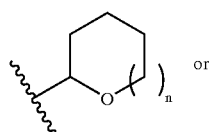 or (h)

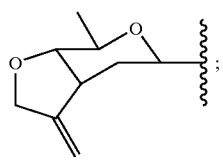

$R^{10}$ is: C(O)H;
$R^{11}$ is: H; and
$X^1$ and $X^2$ are independently H or halo, wherein either $X^1$ or $X^2$ is halo.

4. The compound of claim 1, wherein
R is: $C(O)OR^1$;
$R^{10}$ is: C(O)H;
$R^{11}$ is: H; and
$X^1$ and $X^2$ are independently H or OH, wherein either $X^1$ or $X^2$ is OH.

5. The compound of claim 1, wherein
R is $C(O)NR^2R^3$;
$R^{10}$ is C(O)H;
$R^{11}$ is H; and
$X^1$ and $X^2$ are independently H or OH, wherein either $X^1$ or $X^2$ is OH.

6. The compound of claim 1, wherein
R is: $C(O)R^4$;
$R^{10}$ is: C(O)H;
$R^{11}$ is: H; and
$X^1$ and $X^2$ are independently H or OH, wherein either $X^1$ or $X^2$ is OH.

7. The compound of claim 1, wherein
R is: $C(R^2)OR^5$;
$R^{10}$ is: C(O)H;
$R^{11}$ is: H; and
$X^1$ and $X^2$ are independently H or OH, wherein either $X^1$ or $X^2$ is OH.

8. The compound of claim 1, wherein
R is: $C(R^6)(R^7)(R^8)$;
$R^{10}$ is: C(O)H;
$R^{11}$ is: H; and
$X^1$ and $X^2$ are independently H or OH, wherein either $X^1$ or $X^2$ is OH.

9. The compound of claim 1, wherein
R is

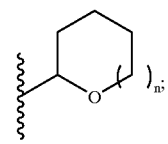

$R^{10}$ is C(O)H;
$R^{11}$ is H; and
$X^1$ and $X^2$ are independently H or OH, wherein either $X^1$ or $X^2$ is OH.

10. The compound of claim 1, wherein
R is

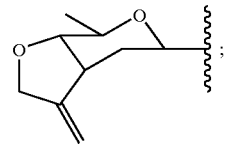

$R^{10}$ is C(O)H;
$R^{11}$ is H; and
$X^1$ and $X^2$ are independently H or OH, wherein either $X^1$ or $X^2$ is OH.

11. The compound of claim 1, wherein
R is

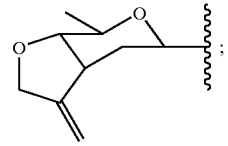

$R^{10}$ is C(O)H;
$R^{11}$ is H; and
$X^1$ and $X^2$ are independently H or Cl, wherein either $X^1$ or $X^2$ is Cl.

12. The compound of claim 1, wherein
R is: $CH(R^6)(R^7)$;
$R^{10}$ is: C(O)H;
$R^{11}$ is: H;
$R^6$ is: (a) H,
  (b) $(C_1-C_{14})$alkyl,
  (c) aryl,
  (d) aryl-$(C_1-C_6)$alkyl,
  (e) $(CH_2)_y CH(OH)(CH_2)_z H$ or
  (g) $(CH_2)_y C(R^7)=CH(CH_2)_z H$;
$R^7$ is: H or $(C_1-C_{14})$alkyl; and
$X^1$ and $X^2$ are independently H or OH, wherein either $X^1$ or $X^2$ is OH.

13. The compound of claim 1, wherein
R[10] is: C(O)H;
R[11] is: H;
R is: (a) $(C_1-C_7)$alkyl,
 (b) aryl-$(C_1-C_6)$alkyl,
 (c) $(CH_2)_y CH{=}CH(CH_2)_z H$,
 (d) $[(C_1-C_6)alkyl]{-}CH_2CH{=}CHCH_2CH_3$ or
 (e) $[(C_1-C_6)alkyl]{-}CH_2CH{=}CH(CH_2)_2CH_3$; and
$X^1$ and $X^2$ are independently H or OH, wherein either $X^1$ or $X^2$ is OH.

14. The compound of claim 1, wherein the compounds are:

| | |
|---|---|
| (1S,3aR,4S,8aS)-6-(acetyloxy)-8a-[(acetyloxy)methyl]-4-formyl-3-isopropyl-7-methyl-4,4a,5,6,7,7a,8,8a-octahydro-1,4-methano-s-indacene-3a(1H)-carboxylic acid | 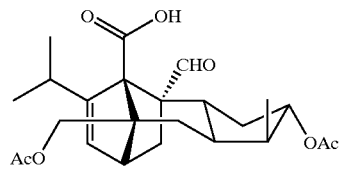 |
| (1S,3aR,4S,8aS)-6-(methoxy)-8a-[(methoxy)methyl]-4-formyl-3-isopropyl-7-methyl-4,4a,5,6,7,7a,8,8a-octahydro-1,4-methano-s-indacene-3a(1H)-carboxylic acid | 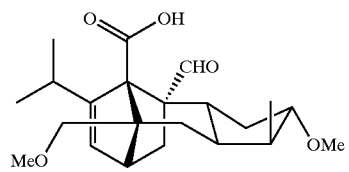 |
| (1S,3aR,4S,8aS)-6-(propoxy)-8a-[(propoxy)methyl]-4-formyl-3-isopropyl-7-methyl-4,4a,5,6,7,7a,8,8a-octahydro-1,4-methano-s-indacene-3a(1H)-carboxylic acid | 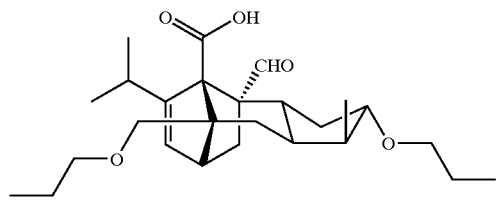 |
| (1R,3aR,4S,8aS)-6-(butoxymethyl)-4-formyl-6-hydroxy-3-isopropyl-7-methyl-4,4a,5,6,7,7a,8,8a-octahydro-1,4-methano-s-indacene-3a(1H)-carboxylic acid | 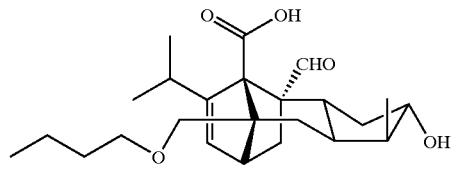 |
| (1R,3aR,4S,8aS)-8a-(butoxymethyl)-6-chloro-4-formyl-3-isopropyl-7-methyl-4,4a,5,6,7,7a,8,8a-octahydro-1,4-methano-s-indacene-3a(1H)-carboxylic acid | 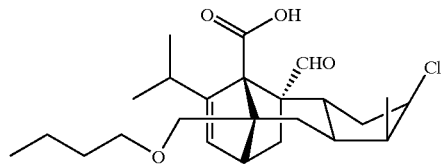 |
| (1R,3aR,4S,8aS)-8a-(butoxymethyl)-6-azido-4-formyl-3-isopropyl-7-methyl-4,4a,5,6,7,7a,8,8a-octahydro-1,4-methano-s-indacene-3a(1H)-carboxylic acid | 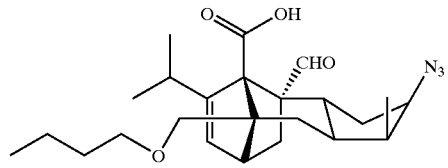 |
| (1R,3aR,4S,8aS)-8a-(butoxymethyl)-4-formyl-6-hydroxy-3-isopropyl-7-methyl-4,4a,5,6,7,7a,8,8a-octahydro-1,4-methano-s-indacene-3a(1H)-carboxylic acid | 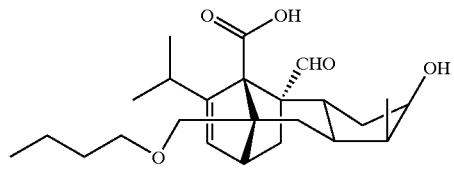 |

-continued (1R,3aR,4S,8aS)-8a-(butoxymethyl)-4-formyl-3-isopropyl-6-methoxy-7-methyl-4,4a,5,6,7,7a,8,8a-octahydro-1,4-methano-s-indacene-3a(1H)-carboxylic acid

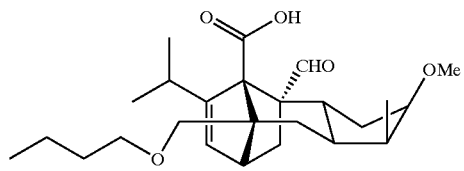

(1R,3aR,4S,8aS)-8a-(butoxymethyl)-6-fluoro-4-formyl-3-isopropyl-7-methyl-4,4a,5,6,7,7a,8,8a-octahydro-1,4-methano-s-indacene-3a(1H)-carboxylic acid

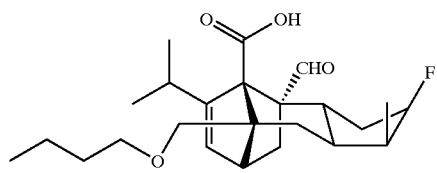

(1R,3aR,4S,8aS)-8a-(butoxymethyl)-6-cyano-4-formyl-3-isopropyl-7-methyl-4,4a,5,6,7,7a,8,8a-octahydro-1,4-methano-s-indacene-3a(1H)-carboxylic acid

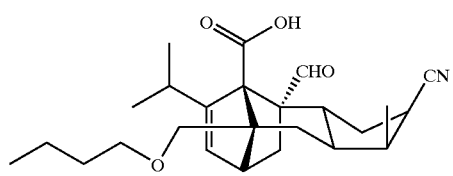

(1R,3aR,4S,8aS)-8a-(hydroxymethyl)-4-formyl-3-isopropyl-6-chloro-7-methyl-4,4a,5,6,7,7a,8,8a-octahydro-1,4-methano-s-indacene-3a(1H)-carboxylic acid

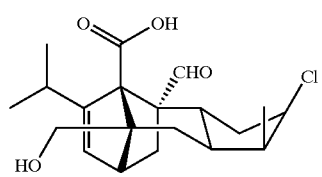

(1R,3aR,4S,8aS)-6-chloro-4-formyl-3-isopropyl-7-methyl-8a-{[(7-methyl-3-methylenehexahydro-2H-furo[2,3-c]pyran-5-yl)oxy]methyl}-4,4a,5,6,7,7a,8,8a-octahydro-1,4-methano-s-indacene-3a(1H)-carboxylic acid

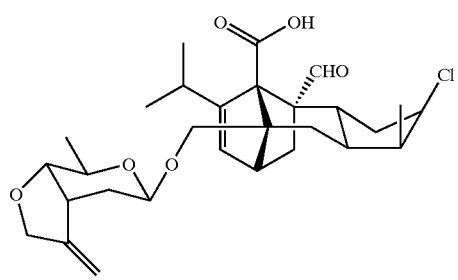

15. A pharmaceutical composition, which comprises a compound of formula I according to claim 1 and a pharmaceutically acceptable carrier.

16. A pharmaceutical formulation comprising a combination of a compound of formula I according to claim 1 and a second therapeutic agent or its pharmaceutically acceptable salt.

17. The pharmaceutical formulation of claim 16, wherein the second therapeutic agent is a compound selected from the group consisting of an azole, polyene, purin uncleotide inhibitor, pneumocandin derivative, echinocandin derivative, elongation factor inhibitor, and immunomodulating agent.

18. The pharmaceutical formulation of claim 17, wherein the second therapeutic agent is a compound selected from the group consisting of intraconazole, flucytosine, fluconazole, and amphotericin B.

19. An agrochemical composition, which comprises a compound of formula I according to claim 1 and an agriculturally acceptable carrier.

20. An agrochemical composition, which comprises a compound of formula I according to claim 1 and a second active ingredient selected from the group consisting of herbicides, insecticides, bactericides, nematocides, molluscicides, growth regulators, micronutrients, fertilizers, and fungicides.

21. A method for the treatment or prevention of fungal infection in a mammal, which comprises administering to said mammal therapeutically effective amounts of a compound of formula I according to claim 1.

22. A method for the treatment or prevention of fungal infection in a mammal, which comprises administering to said mammal therapeutically effective amounts of a compound of formula I according to claim 1 and a second therapeutic agent selected from the group consisting of an azole, polyene, purin nucleotide inhibitor, pneumocandin derivative, echinocandin derivative, the elongation factor inhibitor, and immunomodulating agent.

23. A method for controlling phytopathogenic fungi, which comprises administering to a plant in need of such control therapeutically effective amounts of a compound of formula I according to claim 1.

24. A method for controlling phytopathogenic fungi, which comprises administering to a plant in need of such control therapeutically effective amounts of a compound of formula I according to claim 1 and a second active ingredient selected from the group consisting of herbicides, insecticides, bactericides, nematocides, molluscicides, growth regulators, micronutrients, fertilizers, and fungicides.

* * * * *